United States Patent [19]

Srinivasan et al.

[11] Patent Number: 6,132,697
[45] Date of Patent: Oct. 17, 2000

[54] RADIOPHARMACEUTICAL COMPOSITIONS CAPABLE OF LOCALIZING AT SITES OF THROMBUS

[75] Inventors: Ananthachari Srinivasan, St. Charles, Mo.; Larry P. Feigen, Wauconda, Ill.; Daniel Lee Flynn, Clarkson Valley, Mo.; Jeffery Alan Zablocki, LaFayette, Colo.; Philip Needleman, Creve Coeur, Mo.; Michelle A. Schmidt, Belleville, Ill.

[73] Assignee: G. D. Searle & Co., Chicago, Ill.

[21] Appl. No.: 08/870,042

[22] Filed: Jun. 5, 1997

Related U.S. Application Data

[60] Provisional application No. 60/019,513, Jun. 10, 1996.

[51] Int. Cl.$^7$ .......................... A61K 51/00; A61K 38/00; C07F 5/00
[52] U.S. Cl. .......................... 424/1.69; 424/1.65; 534/10; 534/12; 534/14; 530/300; 530/323
[58] Field of Search .................. 424/1.69, 1.65, 424/1.41, 9.36, 9.361; 534/10, 12, 14, 15, 16; 530/300, 323; 560/35, 13; 556/465; 562/440; 206/223, 569, 570

[56] References Cited

U.S. PATENT DOCUMENTS

| | | | |
|---|---|---|---|
| 5,120,526 | 6/1992 | Fritzberg et al. | 424/1.1 |
| 5,220,050 | 6/1993 | Bovy et al. | 514/357 |
| 5,310,536 | 5/1994 | Srinivasam | 424/1.65 |
| 5,330,738 | 7/1994 | Nosco | 424/1.65 |
| 5,332,726 | 7/1994 | Klein et al. | 514/18 |
| 5,344,957 | 9/1994 | Bovy et al. | 560/35 |
| 5,453,440 | 9/1995 | Bovy et al. | 514/533 |
| 5,556,609 | 9/1996 | Zamora | 424/1.69 |
| 5,662,885 | 9/1997 | Pollak et al. | 424/1.69 |

FOREIGN PATENT DOCUMENTS

| | | | |
|---|---|---|---|
| 0 502 536 A1 | 9/1992 | European Pat. Off. | C07K 5/02 |
| WO 92/15607 | 9/1992 | WIPO | C07K 5/06 |
| WO 93/23085 | 11/1993 | WIPO | A61K 49/02 |
| WO 94/05694 | 3/1994 | WIPO | C07K 5/06 |
| WO 94/22494 | 10/1994 | WIPO | A61K 49/02 |
| WO 95/01371 | 1/1995 | WIPO | C07K 7/06 |
| WO 95/33496 | 12/1995 | WIPO | A61K 51/08 |
| WO 95/33497 | 12/1995 | WIPO | A61K 51/08 |

OTHER PUBLICATIONS

Vanoli et al., "Fresh Thrombus Imaging With A New Tc–99m Labeled Peptidomimetic", *Journal of Nuclear Medicine, Scientific Abstracts of the 44$^{th}$ Annual Meeting of the Society of Nuclear Medicine*, p 26P, Abstract No. 89, (1997).

Liu et al., "Labeling Cyclic Glycoprotein IIb/IIIa Receptor Antagonists with 99m–Tc by the Preformed Chelate Approach. . . ." *Bioconjugate Chem.*, vol. 7, 196–202, (1996).

Zablocki et al,, "Potent in Vitro and in Vivo Inhibitors of Platelet Aggregation...", *J. Med. Chem.*, 1993, 36, 1811–1819.

Rajopadhye et al., "Synthesis, Evaluation and Tc–99m Complexation of a Hydrazinonicotinyl Conjugate of a GP IIb/IIIa Antagonist...", *Bioorganic & Medicinal Chem. Letters*, vol. 7, No. 8, pp. 955–960, 1997.

*Primary Examiner*—Jose' G. Dees
*Assistant Examiner*—Michael G. Hartley
*Attorney, Agent, or Firm*—Cynthia S. Kovacevic

[57] ABSTRACT

A radiopharmaceutical capable of localizing at a site of thrombus containing activated platelets within a mammalian body is provided wherein the radiopharmaceutical comprises a linear peptidomimetic containing ligand capable of specifically binding to the GPIIb/IIIa integrin receptor of platelets in the thrombus and a radionuclide covalently bound to the peptidomimetic containing ligand. The ligand compositions of the invention are provided complexed with a selected metal radionuclide to form a diagnostic or therapeutic radiopharmaceutical to image a site of thrombus or provide radiotherapy to the site of thrombus, respectively. Methods of imaging a site of thrombus in a mammalian body by administering a diagnostically effective amount of the radiopharmaceutical composition of this invention complexed with a selected diagnostic metal radionuclide and methods of providing therapy to a site of thrombus in a mammalian body by administering a therapeutically effective amount of the radiopharmaceutical composition of this invention complexed with a selected therapeutic metal radionuclide are also provided as well as kits for preparing such radiopharmaceutical compositions.

80 Claims, No Drawings

RADIOPHARMACEUTICAL COMPOSITIONS CAPABLE OF LOCALIZING AT SITES OF THROMBUS

The present application claims priority under 35 USC §119 (e) of United States provisional application Ser. No. 60/019,513, filed Jun. 10, 1996.

FIELD OF THE INVENTION

This invention relates generally to radiopharmaceutical compositions and, more specifically, to a radiopharmaceutical composition capable of imaging or providing radiotherapy to sites of thrombus in a warm-blooded individual.

BACKGROUND OF THE INVENTION

During the blood clotting mechanism, platelets rapidly respond to form a thrombus in cooperation with fibrinogen. At the site of injury, platelets bind to fibrinogen which initiates platelet aggregation to form the thrombus. As currently understood, a significant aspect of the aggregation process involves Glycoprotein(gp)IIb/IIIa, a platelet surface integrin which binds fibrinogen and links together activated platelets to form an aggregate.

Deep vein thrombosis (DVT) and pulmonary embolism (PE) are common clinical observations resulting from thrombus formation and are associated with nearly 5 million patients in the United States alone. PE results in over 100,000 deaths per year and patients with DVT formation have a high probablity of PE formation. Several interventional methods using an anticoagulant or fibrinolytic have been utilized to treat DVT and PE, including treatment with heparin, streptokinase or recombinant tissue plasminogen activators. Before these treatments can begin, however, the diagnosis of the condition must be made.

Diagnostic radionuclides have been successfully used to detect various pathological conditions. The method is effective when the radionuclide can be effectively attached to a moiety that can localize to a selected biological site without interfering with the localization or binding of the localizing moiety. In this manner, the rapid identification of these sites becomes possible.

Various approaches for the detection of thrombi have been proposed. Existing non-radionuclide based methods of detecting and diagnosing thrombus formation include contrast venography and ultrasound. A prior knowledge of thrombus formation is highly desirable for either of these methods to be used advantageously and the venography technique is invasive. Radiolabeled thrombin inhibitors, plasmin, plasminogen activators such as TPA, heparin, fibronectin and anti-platelet monoclonal antibodies have also variously been proposed and used to radioimage thrombi. These radiolabelled approaches, however, present numerous disadvantages which limit their desirability as a diagnostic radiopharmaceutical. Most significantly, a long waiting period between injection and imaging is typically associated with these radiolabelled compositions which is considered undesirable in terms of patient comfort and ease of use.

Hence, a need exists for a diagnostic composition that rapidly locates sites of thrombus in vivo to facilitate a determination as to whether further diagnostic and/or therapeutic treatment is necessary or to provide a quick and reliable means to follow the course of prior treatment of a thrombus.

SUMMARY OF THE INVENTION

The present invention is directed to a radiopharmaceutical capable of localizing at a site of thrombus containing activated platelets within a mammalian body wherein the radiopharmaceutical comprises a linear peptidomimetic capable of specifically binding to the GPIIb/IIIa integrin receptor of activated platelets in the thrombus and a radionuclide covalently bound to the peptidomimetic.

In one significant aspect of the invention, a ligand composition having the following general formula is provided:

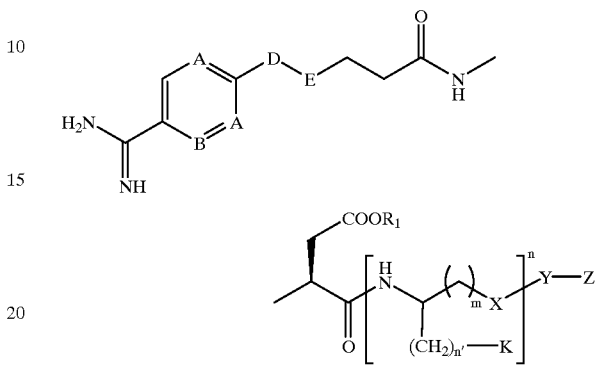

where A is —CH— or —N—, and B is —CH— or —N—, with the proviso that when A is —N—, B is —CH—, and when B is —N—, then A is —CH—; —D—E— is —CH$_2$—CH$_2$—, or —NHCO— with the proviso that when A is —N—, then —D—E is —CH$_2$—CH$_2$—, and when B is —N—, then —D—E is —NHCO—; R$_1$ is hydrogen, lower alkyl, or acyloxyalkyl; K is hydrogen, carboxyl, lower alky, aralkyl, substituted or unsubstituted aromatic, or an alkylene or substituted alkylene substituted with one of the following substituents: primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; X is NH, CO, S, or O; Y is NH, CO, CS, CONH, CSNH, NHCO, NHCS, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH, with the proviso that X and Y are different except when X is S, and when X is O, Y is CO, and when X is S, Y is S, CO or CS, and when X is NH, Y is CO, CONH, CSNH, CONHØ(CH$_2$)$_{1-4}$CONH, CONH(CH$_2$)$_{1-4}$CONH, CSNHØ(CH$_2$)$_{1-4}$CONH, or CSNH (CH$_2$)$_{1-4}$CONH, and when X is NH, Y is not NH, NHCO or NHCS, and when X is CO, Y is NH, O or S, and when X is CO, Y is not CO, CS, CONH, CSNH, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH; n is 0–5; n' is 0 or 1; m is 0–10; and Z is a metal binding group capable of covalently binding a radionuclide.

In a further significant aspect of the invention, the ligand compositions of the invention as described above are provided complexed with a selected metal radionuclide to form a diagnostic or therapeutic radiopharmaceutical. When complexed with a diagnostic radionuclide the composition is capable of imaging a site of thrombus and when complexed with a therapeutic radionuclide the composition is capable of providing radiotherapy to the site of thrombus.

Also provided are methods of imaging a site of thrombus in a mammalian body by administering a diagnostically effective amount of the radiopharmaceutical composition of this invention complexed with a selected diagnostic metal radionuclide in a pharmaceutically acceptable carrier and methods of providing therapy to a site of thrombus in a mammalian body by administering a therapeutically effective amount of the radiopharmaceutical composition of this invention complexed with a selected therapeutic metal radionuclide in a pharmaceutically acceptable carrier.

The invention also provides kits for preparing radioimaging or radiotherapeutic compositions that include the ligand compositions of the invention and the reagents necessary to produce a radiolabelled ligand composition. Kits for labeling with the selected radionuclide are comprised of a container containing a selected amount of the ligand composition in a pharmaceutically acceptable carrier and a sufficient amount of the other reagents necessary to label the ligand composition, such as a reducing agent.

Among the many objects and advantages of the present invention include the provision of a radiopharmaceutical composition that is capable of selectively imaging or providing therapy to sites of thrombus and that rapidly clears from the blood; the provision of such a composition comprising a radiolabelled, linear peptidomimetic that inhibits platelet aggregation; and the provision of such compositions that are useful as diagnostic or therapeutic agents for thrombus imaging or therapy at sites of thrombus including embolism, deep vein thrombosis, cerebral vascular thrombus, coronary vascular thrombus, and peripheral arterial thrombus.

DETAILED DESCRIPTION OF THE INVENTION

According to the present invention, it has been discovered that certain linear, peptidomimetic antagonists of GPIIb/IIIa can be labeled with a radionuclide without compromising the ability of the peptidomimetic to localize at the site of the thrombus. The compositions are relatively small in size, approximately 1000–3000 daltons, and can be readily produced. Moreover, the compositions are not immunogenic and clear rapidly from the circulating blood. This feature permits rapid imaging of thrombi with little background interference which could complicate a diagnosis.

The ligand compositions described herein comprise a linear peptidomimetic region that is capable of binding to activated platelets and a region capable of binding a metal, preferably a metal radionuclide. Surprisingly, the presence of a metal binding region and a metal radionuclide complexed thereto does not adversely affect the ability of the linear peptidomimetic region to localize at the activated platelets.

In one aspect of the invention, a linear peptidomimetic composition capable of localizing at or binding to activated platelets incorporating a metal binding group is provided and has the following general formula:

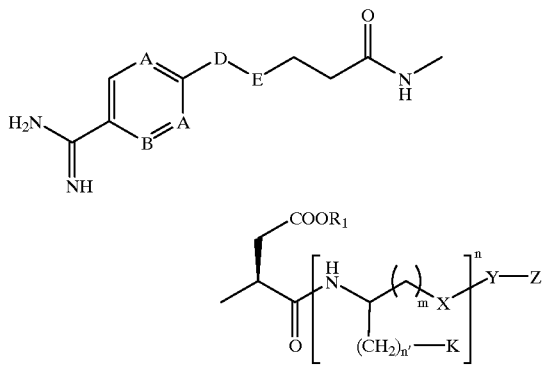

where A is —CH— or —N—, and B is —CH— or —N—, with the proviso that when A is —N—, B is —CH—, and when B is —N—, then A is —CH—; —D—E— is —CH$_2$—CH$_2$—, or —NHCO— with the proviso that when A is —N—, then —D—E is —CH$_2$—CH$_2$—, and when B is —N—, then —D—E is —NHCO—; R$_1$ is hydrogen, lower alkyl, or acyloxyalkyl; K is hydrogen, carboxyl, lower alkyl, aralkyl, substituted or unsubstituted aromatic, or an alkylene or substituted alkylene substituted with one of the following substituents: primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; X is NH, CO, S, or O; Y is NH, CO, CS, CONH, CSNH, NHCO, NHCS, CONHØ(CH2)$_{1-4}$CONH, CONH(CH$_2$)$_{1-4}$CONH, CSNHØ(CH$_2$)$_{1-4}$CONH, or CSNH (CH$_2$)$_{1-4}$CONH, with the proviso that X and Y are different except when X is S, and when X is O, Y is CO, and when X is S, Y is S, CO or CS, and when X is NH, Y is CO, CONH, CSNH, CONHØ(CH$_2$)$_{1-4}$CONH, CONH(CH$_2$)$_{1-4}$CONH, CSNHØ(CH$_2$))$_{1-4}$CONH, or CSNH(CH$_2$)$_{1-4}$CONH, and when X is NH, Y is not NH, NHCO or NHCS, and when X is CO, Y is NH, O or S, and when X is CO, Y is not CO, CS, CONF, CSNH, CONHØ (CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH; n is 0–5; n' is 0 or 1; m is 0–10; and Z is a metal binding group capable of covalently binding a radionuclide.

As used herein, the term "lower alkyl", either alone or within other terms such as phenylalkyl and alkyloxycarbonyl, embraces a linear or branched chain saturated hydrocarbon radical having 1–6 carbon atoms. Illustrative of such radicals are methyl, ethyl, propyl, 1-methylethyl, butyl, 2-methylpropyl, 1-methylpropyl, 1,1-dimethylethyl, pentyl and hexyl. The term "alkylene", either alone or within other terms, embraces linear or branched chain alkene radicals having 1–6 carbon atoms. Illustrative of such radicals are emthylene, ethylene, propylene, butylene, propylene and hexalene.

The metal binding group Z of the ligand compositions described is capable of covalently binding a selected radionuclide thereto. The metal binding group is coupled to or incorporated in the peptidomimetic in a manner that does not interfere or adversely affect the binding properties or specificity of the peptidomimetic. The use of various metal binding groups for radiolabeling compounds is well known in the art. Suitable metal binding groups generally include those which contain a tetradentate ligand for binding the metal radionuclide such as known polyaminocarboxylate, N$_3$S and N$_2$S$_2$ ligands. More particularly, metal binding groups that may be used in conjunction with the peptidomimetics of the present invention include 2,3-bis (mercaptoacetamido)propanoate (U.S. Pat. No. 4,444,690), S-benzoylmercaptoacetylglycylglycylglycine (U.S. Pat. No. 4,861,869), dicyclic dianhydrides such as DTPA and EDTA and derivatives thereof (U.S. Pat. No. 4,479,930), NS chelates containing amino groups to enhance chelation kinetics (U.S. Pat. No. 5,310,536), N$_2$S$_2$ chelates as described in U.S. Pat. No. 4,965,392, the N$_3$S chelates as described in U.S. Pat. No. 5,120,526, and the N$_2$S$_2$ chelates containing cleavable linkers as described in U.S. Pat. No. 5,175,257. All of the patents referred to above and the teachings therein are hereby incorporated by reference hereto.

In a preferred embodiment, Z is defined by the general formula:

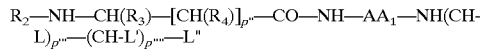

where R$_2$ is COCH(R$_5$)—S—R$_6$; R$_5$ is H, —(CH$_2$)$_p$—R$_7$ ; p is 1–5; R$_7$ is a hydrogen, primary amine, secondary amine, cyclic or acyclic tertiary amine, carboxyl, ester, hydroxyl, ether, thiol, thioether, guanido, or an imine; $R_6$ is a hydrogen, aliphatic or aromatic acyl, acetamidoalkyl, benzamidoalkyl, unsubstituted or substituted tetrahydropyranyl, unsubstituted or substituted tetrahydrofuranyl, or alkoxyalkyl; $R_3$ is $(CH_2)_{p'}$-Q where p' is 0–6, Q is hydrogen, alkylene or substituted alkylene, aryl or substituted aryl group for attachment to Y; $R_4$ is $(CH_2)_s$T where s is 0–6, T is hydrogen, alkylene or substituted alkylene,, aryl or substituted aryl group for attachment to Y; p" is 0,1 if p" is 1 only one of the groups defined under Q or T is attached to Y; $AA_1$ is any natural or unnatural α-amino acid or β-amino acid; L, L'=is a hydrogen, carboxyl, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; p''' is 0–3; p"" is 0–3; L" is a hydrogen, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl.

The metal binding group is coupled to or incorporated into the peptidomimetic by standard methodology known in the field of the invention and may be added at any location on the peptidomimetic provided that the biological activity of the peptidomimetic is not adversely affected.

Illustrative of suitable peptidomimetic containing ligands within the scope of the invention include the following compositions:

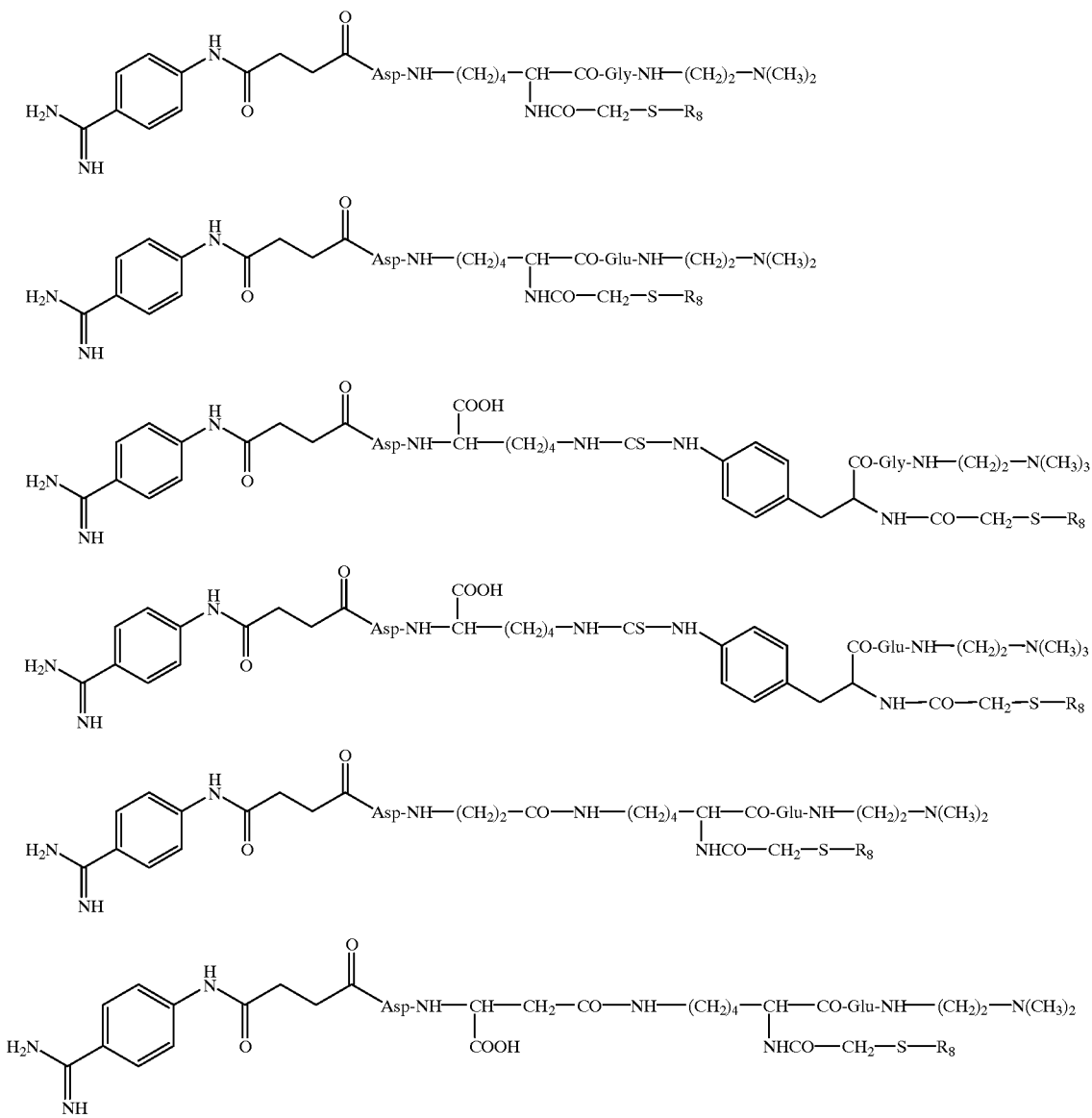

-continued

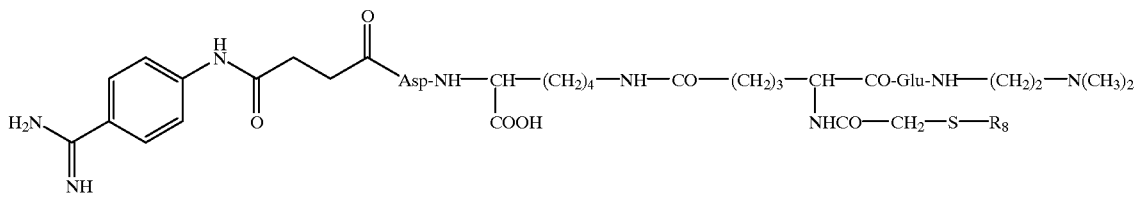

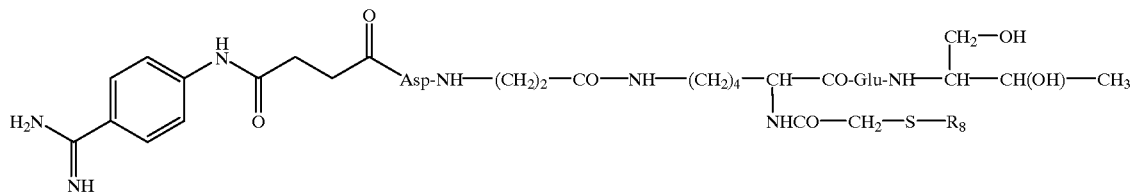

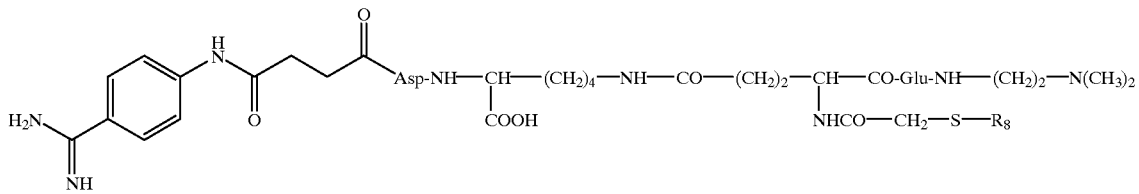

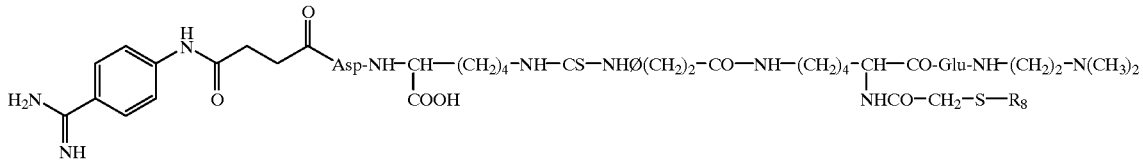

where $R_8$ is a suitable sulfur protecting group. As used herein, a suitable sulfur protecting group is a pharmaceutically acceptable compound capable of preventing potential oxidation of the sulfur or reaction of the sulfur with other reactive groups. Illustrative protecting groups include hydrogen, acetals such as ethoxyethyl, methoxymethyl, substituted and unsubstituted tetrahydrofuranyl, substituted and unsubstituted tetrahydropyranyl, acetamidoalkyl such as acetamidomethyl, acyl such as alkanoyl, benzoyl and substituted benzoyl.

The radiopharmaceutical compositions of the present invention may be complexed with a radionuclide (radiolabeled) by methods known in the art. Briefly, radionuclide complexes may be prepared by reacting a specified amount of the selected composition with a metal salt of the selected radionuclide in the presence of a reducing agent and a transfer agent. Preferred reducing agents include, but are not limited to, dithionite, stannous ion, and ferrous ion. Preferred transfer agents include, but are not limited to, sodium gluconate, sodium tartrate, sodium citrate, and mannitol.

Any radionuclide having diagnostic or therapeutic value can be used as the radiolabel for the compositions of this invention. In a preferred embodiment, the radionuclide is a γ-emitting or β-emitting radionuclide selected from the lanthanide or actinide series of the elements. Positron-emitting radionuclides, e.g. 68 Ga, may also be used.

Suitable γ-emitting radionuclides include those which are useful in diagnostic imaging applications. The Remitting radionuclides preferably have a half-life of from 1 hour to 40 days, preferably from 12 hours to 3 days. Examples of suitable γ-emitting radionuclides include 67Ga, 111In, 99mTc, 169Yb and 186Re. Most preferably, the radionuclide is 99 mTc.

Suitable β-emitting radionuclides include those which are useful in therapeutic applications. Examples include 90Y, 67Cu, 186Re, 188Re, 169Er, 121Sn, 127Te, 143Pr, 198Au, 109Pd, 165Dy, 32P, 142Pr, and 153Sm. The β-emitting radionuclide preferably has a half-life of from 2 hours to two weeks, and more preferably from about 2 hours to 100 hours.

Suitable radiopharmaceutical complexes include the following compositions:

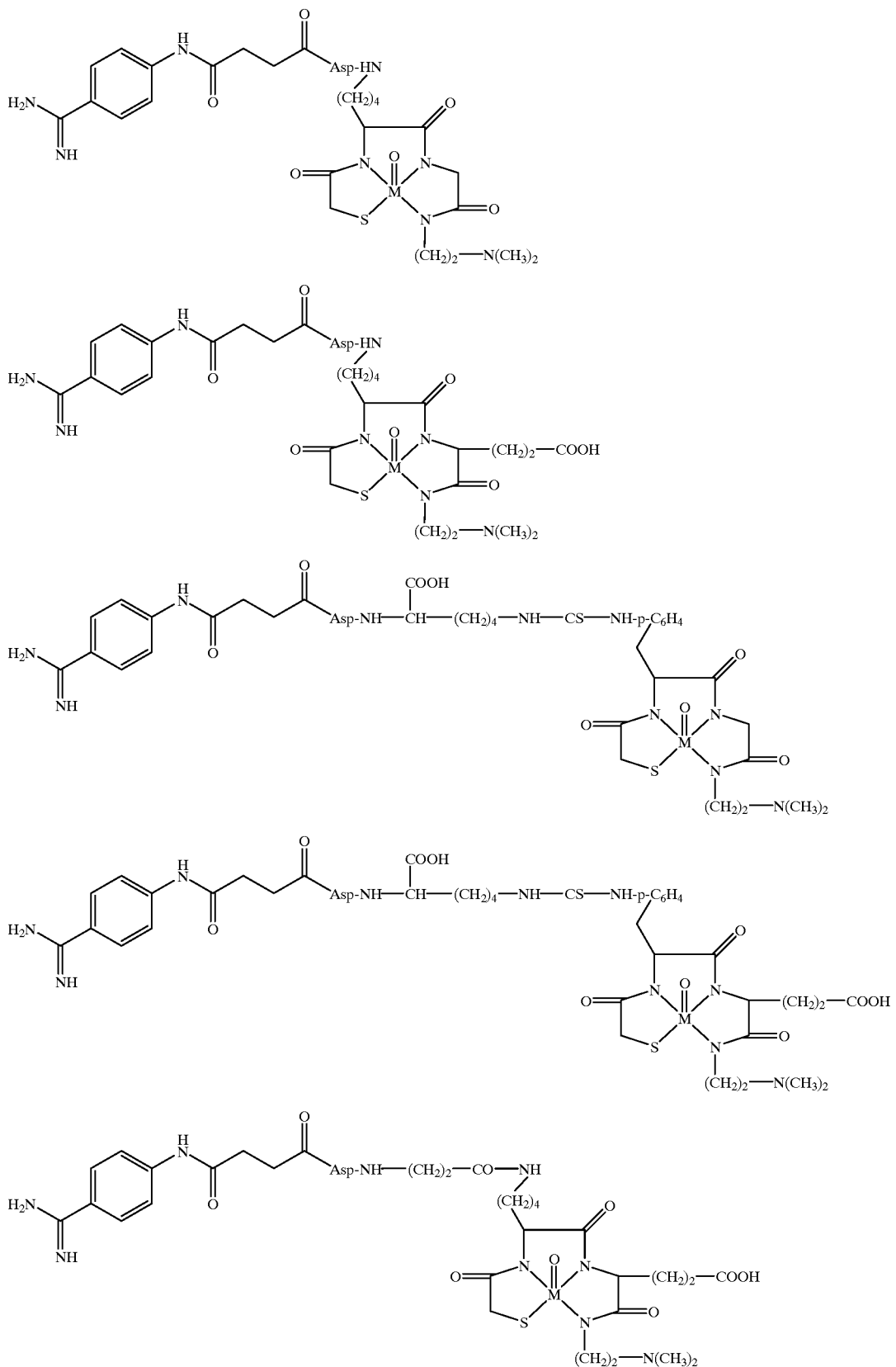

-continued
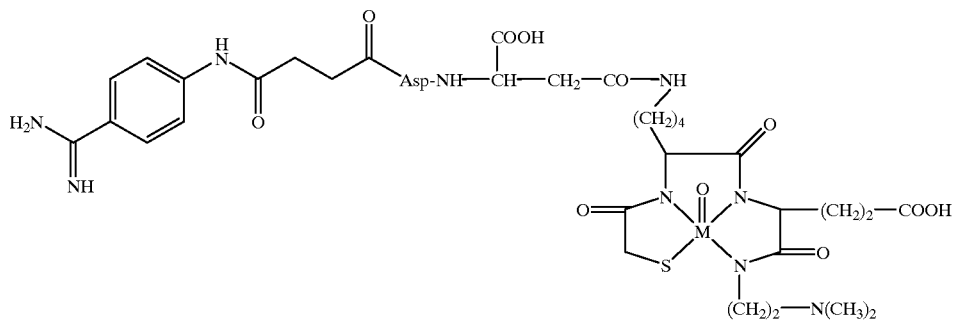
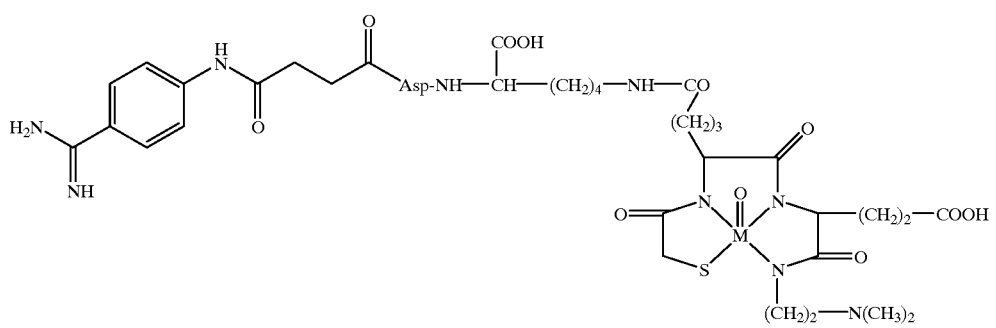
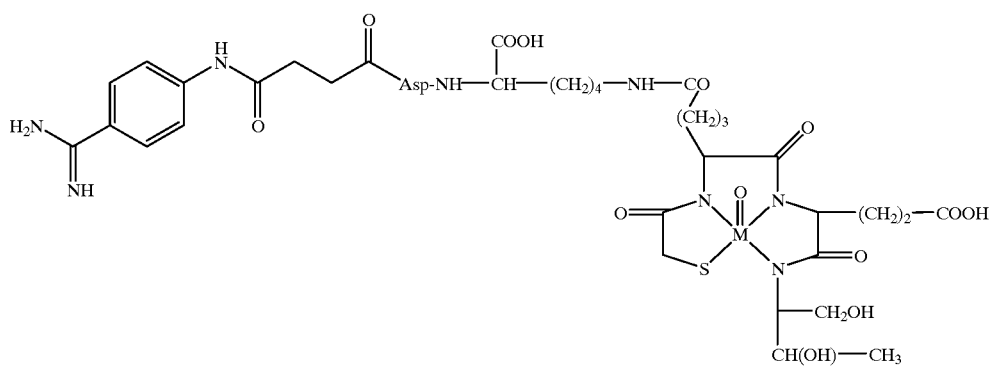
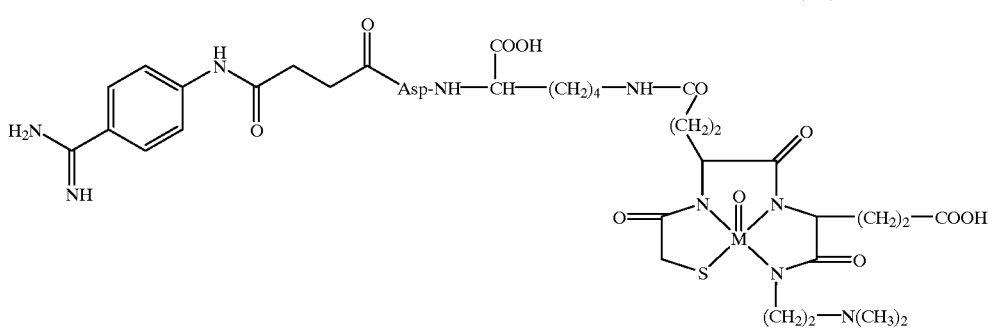
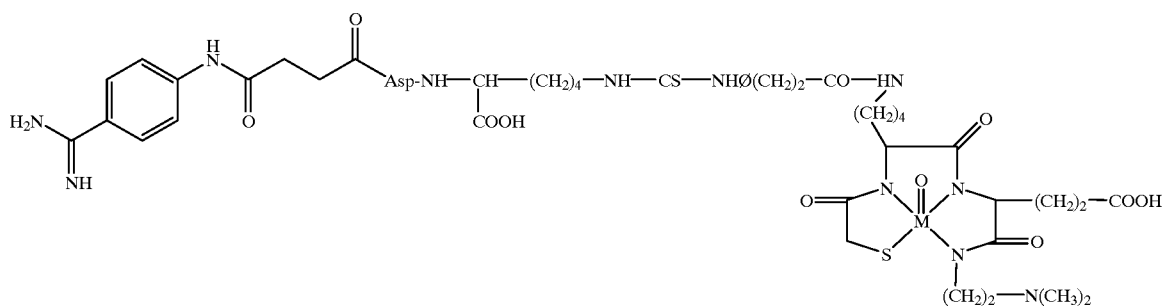

where M is selected from the group consisting of 67Ga, 111In, 99mTc, 169Yb, 186Re 90Y, 67Cu, 186Re, 188Re, 169Er, 121Sn, 127Te, 143Pr, 198Au, 109Pd, 165Dy, 32P, 142Pr, and 153Sm.

The radiolabeled compositions of the invention and their pharmaceutically acceptable salts are useful as a diagnostic imaging agent or in therapeutic applications. The radiolabeled composition is prepared in a pharmaceutically acceptable carrier, e.g. saline or blood plasma, and is administered to an individual in a diagnostically or therapeutically effective amount as determined using standard methods known to those in the art. The carrier may also contain pharmaceutically acceptable adjunct materials such as salts, buffers, preservatives and the like. Preferably, the radiopharmaceutical composition of the present invention is provided in a kit whereby the radionuclide is provided in one container, e.g. a vial, and the composition capable of complexing with the radionuclide is provided in a second container and the contents mixed just prior to administration. The mixture may be heated if necessary to effect complete labelling. The provision of such radiolabeled complexes in kit form and the preparation of the final radiolabeled product are standard and routine in the field of nuclear medicine. The final radiopharmaceutical product should be of high radiochemical purity, preferably greater than 95%, and at least greater than 90%, as determined by standard protocols known in the art.

The radiolabeled complex is prepared to provide a radioactive dose of between about 0.05 mCi and about 40 mCi, preferably about 1 mCi to about 20 mCi, to the individual in accordance with standard radiopharmaceutical dosing determinations. As used herein, "a diagnostically effective amount" means an amount of the radiopharmaceutical sufficient to permit its detection by scintigraphic means and "a therapeutically effective amount" means an amount sufficient to effect a therapeutic treatment at the targeted biological site. The radiolabeled peptides may be administered intravenously in any conventional medium for intravenous injection. Imaging of the biological site may be effected within about one hour post-injection, but may also take place several hours post-injection. Any conventional method of imaging for diagnostic purposes may be utilized.

It is well known in the art that technetium and rhenium form complexes with chemical structures that are identical, but because 99 mTc is produced at tracer levels, one cannot readily perform chemical characterization or in vitro studies on such complexes. The corresponding rhenium (185,187 isotopes) complexes are preferred for structure determination and in vitro assays because they can be obtained in sufficient amount and are non-radioactive. To confirm the structure of the specific embodiments of this invention, each was reacted with perrhenate-185,187 in the presence of stannous ion and an exchange agent, sodium tartarate. The Re-complexes were isolated by reverse phase liquid chromatography and identified by mass spectrometry. Retention times of the rhenium complexes closely match those of the Tc-99m complexes. This ensures the chemical composition of the Tc-99m complexes.

The following examples describe preferred embodiments of the invention. Other embodiments within the scope of the claims herein will be apparent to one skilled in the art from consideration of the specification or practice of the invention as disclosed herein. It is intended that the specification, taken together with the examples, be considered exemplary only, with the scope and spirit of the invention being indicated by the claims. In the Examples that follow, all solvents and reagents used were as supplied from the vendors without further purification. Amino acid derivatives were purchased commercially. Thin layer chromatography (TLC) was performed with 1×3 in. Whatman $SiO_2$ and $C_{18}$ plates with fluorescent indicators. TLC visualization was accomplished using UV light, iodine, and/or vanillin stain. HPLC analyses and purification were performed on Waters systems using either Nova-Pak or Vydac $C_{18}$ columns. NMR spectra were recorded on a 300 MHZ Varian Gemini spectrometer while all mass spectra were recorded on a Finnigan TSQ 500 instrument using electrospray ionization. The standard three letter abbvreviations for amino acids and the following abbreviations have been used in the Examples:

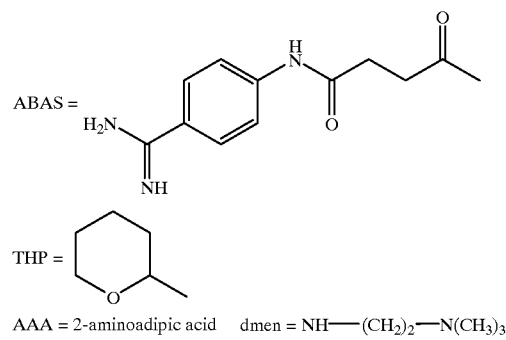

AAA = 2-aminoadipic acid    dmen = NH—$(CH_2)_2$—$N(CH_3)_3$

The compositions of the present invention may be synthesized either in a sequential manner or by segment condensation methodology as further described below.

EXAMPLE 1

This Example describes the stepwise preparation of the compound having the formula

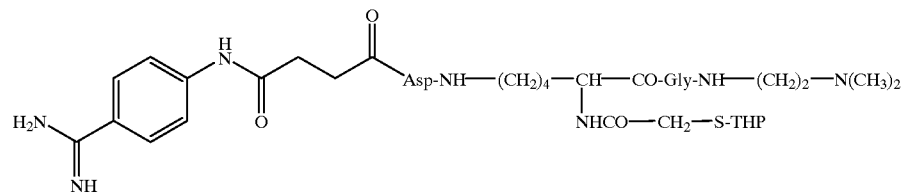

Step a

N-α-Boc-L-Asp(β-t-Bu)-ε-L-Lys(α-Cbz)-OH

Boc-Asp(β-OtBu)—NH$(CH_2)_4$—CH(NH-Cbz)—COOH

N-α-Cbz-L-Lysine (7.25 g, 25.9 mmol) was suspended in a mixture of 1 N sodium bicarbonate (65 mL) and dioxane (65 mL). The N-hydroxysuccinimide ester of N-Boc-L-Asp (β-t-Bu) (10.0 g, 25.9 mmol) in dioxane was subsequently added, and the reaction was permitted to stir overnight at room temperature before concentrating under reduced pressure. The remaining aqueous layer was acidified to pH 3 with 1 N HCl, and the product was extracted into ethyl acetate. The combined organic layer was washed with water (2x) and brine before drying over anhydrous magnesium sulfate. Filtration and evaporation of the solvent under reduced pressure revealed a white foam (12.6 g, 88% yield). TLC (10% MeOH/CH$_2$Cl$_2$) showed only one spot, so no further purification was required. $^1$H NMR (CDCl$_3$) δ8.05 (br m, 1H, amide NH), 7.27 (m, 5H, aromatic), 5.74 (d, 1H, carbamate NH), 5.06 (dd, 2H, benzylic CH$_2$), 4.41 (m, 1H, α-H), 4.39 (m, 1H, α-H), 3.12–3.67 (m, 2H, CH$_2$N), 2.58–2.75 (m, 2H, CH$_2$CO$_2$—), 1.25–1.83 (m, 6H, 3 CH$_2$'s), 1.39 (s, 9H, C(CH$_3$)$_3$), 1.37 (s, 9H, C(CH$_3$)$_3$); $^{13}$C NMR (CDCl$_3$) δ175, 172, 171, 156, 155, 136, 129, 128, 81.7, 80.5, 66.9, 53.5, 38.8, 37.3, 31.4, 28.5, 28.0, 27.8, 21.8, 13.9; Mass Spec. (ESI) 552 (M+1, 100%).

Step b

N-Boc-L-Asp(β-t-Bu)-ε-L-Lys)α-Cbz)-Gly-dmen

Boc-Asp (β-OtBu)—NH—(CH$_2$)$_4$—CH—(NH-Cbz)—CO—Gly—NH—(CH$_2$)$_2$—N(CH$_3$)$_2$

N-Boc-L-Asp(β-t-Bu)-ε-L-Lys(α-Cbz) (12.2 g, 22.1 mmol) and N-hydroxysuccinimide (2.80 g, 24.3 mmol) were dissolved in dichloromethane (250 mL) afterwhich dicyclohexylcarbodiimide (5.47 g, 26.5 mmol) was added. The reaction was permitted to stir overnight at ambient temperature before filtering to remove the dicyclohexylurea. After diluting with dichloromethane, it was extracted with saturated sodium bicarbonate (3x) and washed with water (1x) and brine (1x) before drying over anhydrous magnesium sulfate. Filtration and evaporation of the solvent under reduced pressure revealed a white foam (12.2 g, 85% yield). This intermediate (4.00 g, 6.17 mmol) was added to a suspension of glycyl-dmen hydrochloride (1.02 g, 5.61 mmol) in acetonitrile (42 mL) in the presence of triethylamine (0.57 g, 5.61 mmol). The reaction was continued overnight at ambient temperature before diluting with ethyl acetate. The organic layer was extracted with saturated sodium bicarbonate (3x) and washed with brine before drying over anhydrous magnesium sulfate. Filtration and evaporation of the solvent under reduced pressure revealed an off-white foam. It was redissolved in 30% acetonitrile/3% acetic acid/water with a small amount of methanol and loaded onto a reverse phase C$_{18}$ column packed with the same solvent system. Isocratic elution with 30% acetonitrile/3% acetic acid/water gave a white foam in 58% isolated yield. R$_f$=0.57 (60% acetonitrile/3% acetic acid/37% water); $^1$H NMR (DMSO-d$_6$) δ8.23 (t, 1H, amide NH), 7.76 (m, 2H, 2 amide NH), 7.49 (d, 1H, carbamate NH), 7.32 (m, 5H, aromatic), 6.93 (d, 1H, carbamate NH), 5.02 (s, 2H, benzylic CH$_2$), 4.23 (m, 1H, α-H), 3.91 (m, 1H, α-H), 3.66 (m, 2H, Gly CH$_2$), 3.20 (m, 2H, CH$_2$N), 3.17 (m, 2H, CH$_2$N), 2.24 (s, 6H, N(CH$_3$)$_2$), 2.04–2.56 (m, 4H, CH$_2$CO$_2$-t-Bu+CH$_2$N), 1.35 (2 s's, 18H, 2 C(CH$_3$)$_3$), 1.13–1.84 (m, 6H, 3 CH$_2$'s), 1.87 (s, 3H, CH$_3$CO$_2$H); $^{13}$C NMR (DMSO-d$_6$) δ173, 171, 170, 169, 157, 156, 137, 129, 128.3, 128.1, 80.3, 78.6, 65.8, 57.5, 55.1, 44.5, 42.3, 36.1, 31.2, 28.7, 28.2, 27.7, 22.8, 21.3.

Step c

N-Boc-L-Asp(β-t-Bu)-ε-L-Lys-Gly-dmen

Boc-Asp (β-OtBu)—NH—(CH$_2$)$_4$—CH(NH$_2$)—CO—Gly—NH—(CH$_2$)$_2$—N(CH$_3$)$_2$

N-Boc-L-Asp(β-t-Bu)-ε-L-Lys(α-Cbz)-Gly-dmen (1.97 g, 2.90 mmol) was dissolved in methanol (25 mL). After flushing with nitrogen, the 10% Pd/C catalyst (0.2 g) was added. The mixture was shaken for 6 hours at ambient temperature under an atmosphere of hydrogen (40 p.s.i.). The reaction was filtered through a pad of Celite, and the filtrate was concentrated under reduced pressure to reveal a white foam. By $^1$H and $^{13}$C NMR, it appeared that a quantitative yield of the diacetate salt 5 was obtained due to the presence of excess acetic acid from the prior purification. $^1$H NMR (CDCl$_3$) δ8.53 (t, 1H, amide NH), 8.36 (t, 1H, amide NH), 6.97 (t, 1H, amide NH), 5.89 (d, 1H, J=8.2 Hzm, carbamate NH), 4.41 (m, 1H, α-H), 3.86 (m, 2H, Gly CH$_2$), 3.64 (m, 1H, a-H), 3.52 (m, 2H, CH$_2$N), 3.12–3.41 (m, 2H, CH$_2$N), 2.97 (t, 2H, CH$_2$N), 2.61 (s, 6H, N(CH$_3$)$_2$), 2.55–2.58 (m, 2H, CH$_2$CO$_2$tBu), 1.94 (s, 6H, 2CH$_3$CO$_2$H), 1.39 (s, 9H, C(CH$_3$)$_3$), 1.38–1.81 (m, 6, 3 CH$_2$'s); $^{13}$C NMR (CDCl$_3$) δ177.4, 177.3, 172, 171, 170, 158, 81.4, 80.2, 57.0, 54.1, 43.7, 42.6, 38.7, 37.6, 35.1, 32.4, 28.6, 28.1, 27.8, 22.2, 22.0.

Step d

N-Boc-L-Asp(β-t-Bu)-ε-L-Lys(α-(S-THP-mercaptoacetyl))-Gly-dmen

Boc-Asp(β-OtBu)—NH—(CH$_2$)$_4$—CH—CO-Gly-NH—(CH$_2$)$_2$-N(CH$_3$)$_2$
|
NHCO—CH$_2$—S-THP

N-Boc-L-Asp(β-t-Bu)-ε-L-Lys-Gly-dmen 2 AcOH (1.54 g, 2.32 mmol) and the N-hydroxysuccinimide ester of S-THP-mercaptoacetic acid (0.66 g, 2.43 mmol) were dissolved in dichloromethane (40 mL) in the presence of triethylamine, and the reaction was continued overnight at ambient temperature. The reaction was subsequently diluted with dichloromethane and extracted with water (1x) and saturated sodium bicarbonate (3x) and washed with brine before drying over anhydrous magnesium sulfate. Filtration and evaporation of the solvent under reduced pressure revealed a glassy solid (1.1 g, 69% yield) which was deemed of sufficient purity; no further purification was necessary. $^1$H NMR (CDCl$_3$) δ7.60 (t, 1H, amide NH), 7.49 (m, 1H, amide NH), 6.94 (m, 1H, amide NH), 5.74 (d, 1H, carbamate NH), 4.84 (m, 1H, S—CH—O), 4.39 (m, 1H, a-H), 4.21 (m, 1H, a-H), 3.10–4.01 (m's, 10H, Gly CH$_2$+2 CH$_2$N+OCH$_2$+SCH$_2$CO), 2.78 (m, 2H, CH$_2$CO$_2$tBu), 2.59 (m, 2H, CH$_2$N), 2.34 (s, 3H, NCH$_3$), 2.32 (s, 3H, NCH$_3$), 1.41 (s, 9H, OC(CH$_3$)$_3$), 1.40 (s, 9H, OC(CH$_3$)$_3$), 1.19–2.01 (m, 12H, 6 CH$_2$'s); Mass Spec. (ESI) 545 (M+1, 100%), 273 ((M+2)/2, 20%).

Step e

L-Asp-ε-L-Lys(α-(S-THP-mercaptoacetyl))-Gly-dmen

Asp-NH—(CH$_2$)$_4$—CH—CO-Gly-NH—(CH$_2$)$_2$—N(CH$_3$)$_2$
|
NHCO—CH$_2$—S-THP

N-Boc-L-Asp(β-t-Bu)-ε-L-Lys(α-(S-THP-mercaptoacetyl))-Gly-dmen (40 mg, 0.057 mmol) was dissolved in 1:1 TFA/dichloromethane (0.5 mL each). The reaction was stirred for 5 hours at room temperature before removing the solvent under reduced pressure. The orange, oily residue was purified by reverse phase C$_{18}$ with a 3% acetic acid/water mobile system (29 mg, 76% yield). Mass Spec. (ESI) 547 (M+1, 100%), 274 ((M+2)/2, 20%); $^1$H NMR (D$_2$O) δ4.21 (m, 1H, S—CH—O), 3.90 (m, 1H a-H), 3.55 (m, 1H, a-H), 2.86 (s, 6H, N(CH$_3$)$_2$), 2.71–3.33 (m's, 14H, Gly CH$_2$+CH$_2$CO$_2$H+2 CH$_2$N+CH$_2$N(CH$_3$)$_2$+S—CH$_2$—CO+CH$_2$O), 2.01 (s, 6H, 2 CH$_3$CO$_2$H), 1.30–2.00 (m's, 12H, 6 CH$_2$'s).

Step f
BAS-L-Asp-ε-L-Lys(α-(S-THP-mercaptoacetyl))-Gly-dmen

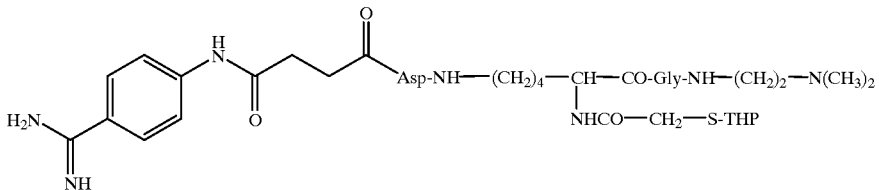

The hydrochloride salt of aminobenzamidinosuccinate (81 mg, 0.30 mmol) was added to dry DMF (4 mL) followed by N-methylmorpholine (30 mg, 0.30 mmol) and isobutyl chloroformate (41 mg, 0.30 mmol) at 0° C. under nitrogen. After stirring for 5 minutes, a solution of L-Asp-e-L-Lys(a-(S-THP-mercaptoacetyl))-Gly-dmen (200 mg 0.30 mmol) and N-methylmorpholine (91 mg, 0.90 mmol) in DMF (2 mL) was added. Stirring was continued for 2 hours after-which the solvent was removed under reduced pressure. The residue was purified by reverse phase $C_{18}$ flash chromatography using 3% acetic acid/water as an isocratic eluent. Mass Spec. (ESI) 764 (M+1, 5%), 382 ((M+2)/2, 100%); H NMR ($D_2O$) δ7.69 (dd, 4H, p-substituted aromatic), 4.58 (m, 1H, S—CH—O), 4.19 (m, 1H, a-H), 3.10–4.00 (m's 13H's, 1 a-H+Gly $CH_2$+2 $CH_2N+CH_2NMe_2+OC$—$CH_2$—$S+OCH_2$), 2.86 (s, 6H, $N(CH_3)_2$), 2.70 (m's 6H, $OC(CH_2)_2CO+CH_2CO_2H$), 2.01 (s, 6H, 2 $CH_3CO_2H$), 1.20–1.97 (m's, 12H, 6 $CH_2$'s).

EXAMPLE 2

This Example describes the radiolabeling of the compound of Example 1 with Tc-99m and a kit formulation.

Method A: Tc-99m labeling was performed using a commercially available Merck-Frosst kit. The kit components were dissolved in 1 mL of water. In a separate vial containing 1 mL pertechnetate (10–100 mCi) from commercially available generator, 100 mL of the solution from Merck-Frosst kit was added and the solution was allowed to stand for 15 minutes. To this solution 30–100 mg of the above derivatives were added and the solution was heated at 75–100° C. for 15–20 minutes. The solution was ready for administration after filtration through a sterile filter.

Method B: Alternatively the componets that are present in the Merck-Frosst kit (gluconate salts, $SnCl_2$) can be added individulally to form the kit.

Compound in Example 1 was radiolabelled with Tc-99m according to the procedure described in Method A.

EXAMPLE 3

This Example describes the labelling of the compound of Example 1 with a non-radioactive rhenium 185,187 isotope to confirm the composition of the final composition.

The composition of the Re-complexes were confirmed by mass spectra (m/e 880 (M+1).

EXAMPLE 4

This Example describes Platelet Aggregation Inhibition Assays of the compound of Example 2 to illustrate that the compound binds to GPIIb/IIIa receptors when radiolabelled.

Healthy aspirin free donors were randomly selected from a pool of volunteers. The harvesting of platelet rich plasma and subsequent ADP induced platelet aggregation assays were performed as described in Zucker, M. B. "Platelet Aggregation Measured by the Photometric Method", Methods in Enzymology 169 (1989):117–133. Standard venipuncture techniques using butterfly allowed the withdrawal of 45 mL of whole blood into a 60 mL syringe containing 5 mL 3.8% trisodium citrate. Following thorough mixing in the syringe, the anti-coagulated whole blood was transferred to a 50 mL conical polyethylene tube. The blood was centrifuged at room temperature for 12 minutes at 200xg to sediment non-platelet cells. Platelet poor plasma was obtained from a second centrifugation of the remaining blood at 2000xg for 15 minutes. Platelet counts are typically 300,000 to 500,000 per microliter. Platelet rich plasma (0.45 mL) was aliquoted into siliconized cuvettes and stirred (1100 rpm) at 37° C. for 1 min. prior to adding 50 mL of prediluted test compound. After 1 minute of mixing, aggregation was initiated by the addition of 50 mL of 200 mM of ADP. Aggregation was recorded for 3 minutes in a Payton dual channel aggregometer (Payton Scientific, Buffalo, N.Y.). The percent inhibition of maximal response (saline control) for a series of test compound dilutions was used to determine a dose response curve. The compounds were tested in duplicate and half-maximal inhibition ($IC_{50}$) was calculated graphically from the dose response curve.

During these studies, $IC_{50}$ values were obtained for both the parent molecules as well as the corresponding Re-185, 187 complexes.

EXAMPLE 5

This study was designed to evaluate the biodistribution pattern of the compound of Example 2 to determine the clearance profile from blood, route of excretion and in vivo stability of the complex by HPLC analysis of urine samples, in a rat model.

The compound of Example 2 was injected (25mL, 1.5–3.5 mCi/mL) into Sprague-Dawley rats. Groups of three animals were sacrificed at the time points indicated below to determine the amount of radioactivity remained in the organs. Results: (to be filled)

EXAMPLE 6

This example describes the stepwise preparation of a composition having the structure:

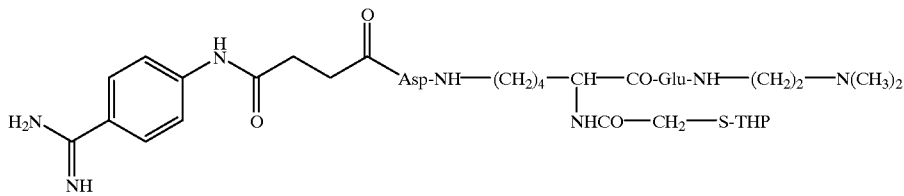

Step a
ABAS-Asp(β-OtBu)—OH

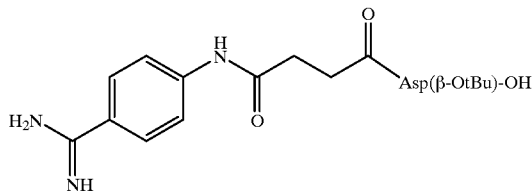

Aminobenzamidinosuccinic acid hydrochloride (500 mg, 1.84 mmol) was suspended in dry DMF (25 mL) under an atmosphere of nitrogen. N-methylmorpholine (186 mg, 1.84 mmol, 0.20 mL) and isobutyl chloroformate (251 mg, 1.84 mmol, 0.24 mL) were added after cooling the reaction to 0° C. Stirring was continued at 0° C. for one half hour before adding a suspension of L-Asp(β-t-Bu) (324 mg, 1.84 mmol) and N-methylmorpholine (0.20 mL) in DMF (12 mL). The reaction was subsequently stirred at ambient temperature overnight. The solvent was removed under reduced pressure, and the residue was dissolved in 3% acetic acid/water. The solution was loaded onto a reverse phase $C_{18}$ column packed with the same solvent system. Initially, 3% acetic acid/water was used to elute unreacted ABAS followed by 10% acetonitrile/3% acetic acid/water to elute the desired product. Evaporation of the appropriate fractions revealed an off-white solid (650 mg, 76% yield). Mass Spec. (ESI) 407 (M+1, 100%); $^1$H NR (DMSO-$d_6$) δ11.3 (br s, 1H), 10.4 (s, 1H, C=NH), 8.81 (br s, 1H), 7.75 (m, 4H, aromatic), 4.32 (m, 1H, Asp-α-H), 2.42–2.62 (m, 6H, 3 $CH_2$'s), 1.87 (s, 3H, $CH_3CO_2H$), 1.35 (s, 9H, OC($CH_3$)$_3$); $^{13}$C NMR (DMSO-$d_6$) δ175, 173, 172, 170.8, 170.7, 166, 144, 129, 123, 119, 79.5, 50.8, 38.8, 31.9, 30.2, 27.7, 21.5.

Step b
Cbz-L-Glu(γ-t-Bu)-dmen
Cbz-L-Glu-(γ-OtBu)—NH—$(CH_2)_2$—N$(CH_3)_2$ The N-hydroxysuccinimide ester of N-Cbz-L-Glu(γ-t-Bu) (7.70 g, 17.7 mmol) and N,N-dimethylethylenediamine (dmen) (1.56 g, 17.7 mmol) were dissolved in dichloromethane (170 mL), and the reaction was stirred overnight at ambient temperature. The reaction was diluted with dichloromethane, extracted with saturated sodium bicarbonate (3x), and washed with brine before drying over anhydrous magnesium sulfate. Filtration and evaporation of the solvent under reduced pressure revealed a white foam (7.08 g, 98% yield). No purification was necessary. $^1$H NMR (CDCl$_3$) δ7.28 (m, 5H, aromatic), 6.67 (br t, 1H, amide NH), 5.78 (d, J=7.7 Hz, 1H, ZNH), 5.05 (s, 2H, benzylic $CH_2$), 4.17 (m, 1H, Glu α-H), 3.28 (q, 2H, amide, N-$CH_2$), 2.28 (m, 4 H, $CH_2$—$NMe_2$+$CH_2CO_2$), 2.17 (s, 61, N($CH_3$)$_2$), 2.04 (m, 1H, 1 b-H of Glu), 1.88 (m, 1H, 1 b-H of Glu), 1.39 (s, 9H, OC($CH_3$)$_3$); $^{13}$C NMR (CDCl$_3$) d 173, 171, 156, 136, 128.6, 128.2, 128.1, 80.7, 66.8, 57.5, 54.2, 44.9, 36.6, 31.4, 28.0, 27.8.

Step c
L-Glu(γ-t-Bu)-dmen
L-Glu-(γ-OtBu)—NH—$(CH_2)_2$—N$(CH_3)_2$

N-Cbz-L-Glu(g-t-Bu)-dmen (7.00 g, 17.2 mmol) was dissolved in methanol (130 mL). After flushing with nitrogen, 10% Pd/C catalyst (0.7 g) was added. The mixture was shaken for 6 hours at ambient temperature under an atmosphere of hydrogen (40 p.s.i.). The reaction was filtered through a pad of Celite, and the filtrate was concentrated under reduced pressure to reveal a yellow oil in quantitative yield. $^1$H NMR (CDCl$_3$) δ7.37 (br s, 1H, amide NH), 3.32 (m, 3H, Glu α-H+CON$HCH_2$), 2.40 (t, 2H, $CH_2NMe_2$), 2.03 (m, 3H, $NH_2$+1 Glu β-H), 1.76 (m, 1 H, 1 Glu β-H), 1.39 (s, 9H, OC($CH_3$)$_3$); $^{13}$C NMR (CDCl$_3$) δ175, 173, 80.4, 58.0, 54.6, 45.0, 36.3, 31.8, 30.2, 27.8.

Step d
S-Tetrahydropyranyl-mercaptoacetyl-L-Lys(ε-Fmoc)

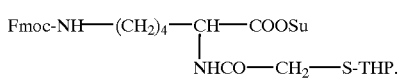

L-Lys(e-Fmoc) (2.70 g, 7.32 mmol) was suspended in a mixture of dioxane (15 mL) and 1 N sodium bicarbonate (15 mL). The N-hydroxysuccinimide ester of S-THP-mercaptoacetic acid (2.00 g, 7.32 mmol) in dioxane (20 mL) was subsequently added, and the reaction was stirred overnight at ambient temperature. The reaction was then concentrated under reduced pressure to remove the dioxane, and the remaining aqueous solution was extracted with ethyl acetate. The ethyl acetate layer was discarded, and the aqueous layer was acidified to pH 3 with 1 N hydrochloric acid. The product was extracted into ethyl acetate; the combined organic layer was washed with water (2x) and brine (1x) before drying over anhydrous sodium sulfate. Filtration and evaporation of the solvent under reduced pressure revealed a white foam. The material was purified on SiO$_2$ using a methanol/dichloromethane gradient to afford 2.60 g of product (67% yield). $^1$H NMR (CDCl$_3$) δ7.72 (d, 2H, aromatic), 7.54 (d, 2H, aromatic), 7.33 (t, 2H, aromatic), 7.22 (t, 2H, aromatic), 6.09 (br s, 1H, amide NH), 5.31 (br m, 1H, carbamate NH), 4.81 (m, 1H, SCHO), 4.29–4.51 (m, 3H), 4.18 (m, 1H), 3.99 (m, 1H), 2.99–3.48 (m, 5H), 1.28–2.05 (m, 12H, 6 $CH_2$'s).

Step e
S-Tetrahydropyranyl-mercaptoacetyl-L-Lys(ε-Fmoc)-OSu.

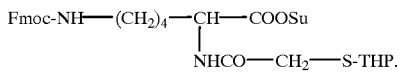

S-Tetrahydropyanyl-mercaptoacetyl-L-Lys(ε-Fmoc) (2.56 g, 4.86 mmol) and N-hydroxysuccinimide (0.62 g, 5.35 mmol) were dissolved in dichloromethane (75 mL). Dicyclohexylcarbodiimide (1.20 g, 5.83 mmol) was subsequently added, and the reaction was stirred at ambient temperature overnight. The reaction was filtered to remove dicyclohexylurea, and the filtrate was diluted with dichloromethane. The organic layer was extracted with saturated sodium bicarbonate (3x) and washed with brine before drying over anhydrous sodium sulfate. Filtration and evaporation of the solvent under reduced pressure revealed a white foam (2.50 g, 87% yield) which was used immediately in the next step. $^1$H NMR (CDCl$_3$) δ7.83 (d, 1H, amide NH), 7.72 (d, 2H, aromatic), 7.68 (d, 1H, amide NH), 7.59 (d, 2H, aromatic), 7.38 (t, 2H, aromatic), 7.29 (t, 2H, aromatic), 5.18 (m, 1H), 4.98 (m, 1H), 4.71 (m, 1H), 4.37 (m, 2H), 4.19 (m, 1H), 3.99 (m, 1H), 3.12–3.52 (m, 4H), 2.79 (s, 4H, COCH$_2$CH$_2$CO), 1.20–2.02 (m, 12H).

Step f
S-Tetrahydropyranyl-mercaptoacetyl-L-Lys(ε-Fmoc)-L-Glu(γ-t-Bu)-dmen

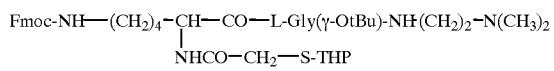

S-Tetrahydropyranyl-mercaptoacetyl-L-Lys(ε-Fmoc) (520 mg, 0.88 mmol) and L-Glu(γ-t-Bu)-dmen (240 mg, 0.88 mmol) were dissolved in dichloromethane (8 mL), and the reaction was stirred overnight at ambient temperature before diluting with dichloromethane. The organic layer was extracted with saturated sodium bicarbonate(3x) and washed with brine (1x) before drying over anhydrous sodium sulfate. Filtration and evaporation of the solvent under reduced pressure revealed a white solid. It was redissolved in 10% methanol/dichloromethane and loaded onto a SiO$_2$ column packed with the same solvent system. Elution was isocratic with 10% methanol/dichloromethane (R=0.51, 10% methanol/dichloromethane). The product-containing fractions were combined and concentrated under reduced pressure to reveal 350 mg of a white solid (51 % yield). $^1$H NMR (CDCl$_3$) δ7.73 (d, 2H, aromatic), 7.58 (d, 2H, aromatic), 7.50 (m, 1H, amide NH), 7.39 (t, 2H, aromatic), 7.29 (t, 2H, aromatic), 7.12 (m, 1H, amide NH), 6.71 (m, 1H, amide NH), 5.19 (m, 1H), 4.79 (m, 1H), 4.37 (m, 4H), 4.19 (m, 1H), 3.99 (m, 1H), 3.00–3.60 (m's, 7H), 2.41 (m, 2H), 2.29 (t, 2H, CH$_2$NMe$_2$), 2.20 (s, 3H, NCH$_3$), 2.10 (m, 2H), 1.48–2.00 (m, 12H), 1.41 (s, 9H, OC(CH$_3$)$_3$).

Step g
S-Tetrahydropyranyl-mercaptoacetyl-L-Lys-L-Glu(γ-t-Bu)-dmen

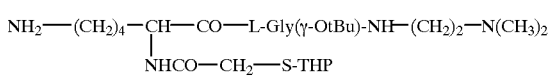

S-Tetrahydropyranyl-mercaptoacetyl-L-Lys(ε-Fmoc)-L-Glu(γ-t-Bu)-dmen (320 mg, 0.41 mmol) was dissolved in DMF (4.1 mL) afterwhich morpholine (0.82 mL) was added. The reaction was stirred for two hours at ambient temperature before removing the solvent under reduced pressure. The residue was redissolved in methanol and filtered to remove the morpholine adduct of dibenzofulvene. The solvent was removed one more time under reduced pressure. The remaining material was purified by dissolving in 30% acetonitrile/water and loading onto a reverse phase C$_{18}$ column packed with the same solvent system. Elution was isocratic with 30% acetonitrile/water (R$_f$=0.14, 30% acetonitrile/5 % acetic acid/water). The product-containing fractions were combined, and the solvent was removed under reduced pressure to reveal a glassy solid (200 mg, 87% yield). $^1$H NMR (CD$_3$OD) δ4.75 (m, 1H), 4.08 (m, 2H), 3.81 (m, 1H), 3.31(m, 1H), 3.09 (m, 4H), 2.48 (t, 2H), 2.22 (t, 2H), 2.09 (m, 2H), 2.01 (s, 6H), 1.88 (m, 1H), 1.12–1.75 (m, 13H), 1.20 (2, 9H); $^{13}$C NMR (CD$_3$OD) δ175, 174.5, 174, 173, 84.2, 84.0, 82.0, 65.9, 59.0, 56.8, 56.0, 45.9, 41.9, 38.0, 32.5, 32.2, 32.1, 32.0, 28.1, 28.0, 26.3, 24.0, 22.9.

Step h

ABAS-L-Asp(β-t-Bu)-ε-L-Lys(α-(S-THP-mercaptoacetyl))-Glu(γ-t-Bu)-dmen

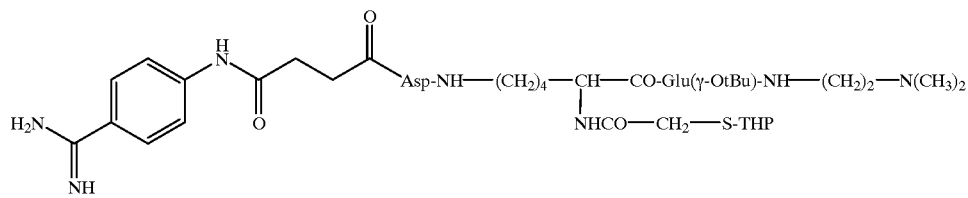

ABAS-L-Asp(β-t-Bu)AcOH (360 mg, 0.77 mmol) was dissolved in DMF (20 mL). N-methylmorpholine (78 mg, 0.77 mmol) and isobutyl chloroformate (105 mg, 0.77 mmol) were added after cooling to 0° C. After stirring for one half hour, the S-THP-mercaptoacetyl-L-Lys-L-Glu(g-t-Bu)-dmen (431 mg, 0.77 mmol) was added in DMF (5 mL). The reaction was subsequently continued at 0° C. for 4 hours before removing the solvent under reduced presssure. The material was purified by reverse phase C$_{18}$ flash chromatography using 30% acetonitrile/3% acetic acid/water as the eluent to afford 220 mg of product (29% yield). Mass Spec. (ESI) 948 (M+H, 10%), 475 ((M+2)/2, 100%); $^1$H NMR (CDCl$_3$) d__10.9 (s, 1H, amidino H), 7.80–8.70 (m's, 6H, amide NH's), 7.61 (m, 4H, aromatic), 4.91 (m, 2H), 4.78 (m, 1H), 3.89–4.23 (m, 3H), 3.05–3.80 (m, 7H), 2.78 (s, 6H), 1.20–2.70 (m, 22H), 1.39 (2 s's, 18H, 2 OC(CH$_3$)$_3$).

Step i
ABAS-L-Asp-ε-L-Lys(α-(S-THP-mercaptoacetyl))-Glu-dmen

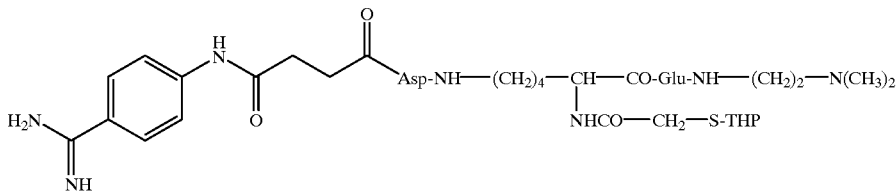

ABAS-L-Asp(β-t-Bu)-ε-L-Lys(a-(S-THP-mercaptoacetyl))-Glu(γ-t-Bu)-dmen (209 mg, 0.21 mmol) was dissolved in formic acid (5 mL). The reaction was stirred overnight at ambient temperature before removing the solvent under reduced pressure. The residue was purified by reverse phase $C_{18}$ chromatography using initially 3% acetic acid/water and finally 10% acetonitrile/3% acetic acid/water as the eluent to give 35 mg of a white powder (20% yield). Mass Spec. (ESI) 836 (M+1, 5%), 418 ((M+2)/2, 100%); $^H$ NMR ($D_2O$) δ7.66 (dd, J=25, 7.1 Hz, 4H), 4.52 (t, 1H), 4.12–4.25 (m, 3H), 3.90 (m, 2H), 3.07–3.56 (m's, 9H), 2.86 (2 s's, 6H), 2.62 (m, 5H), 2.34 (m, 3H), 2,17 (m, 4H), 1.99 (s, $CH_3CO_2H$), 1.20–1.90 (m, 9H).

EXAMPLE 7

The compound of Example 6 was radiolabeled with Tc-99m according to method A described in Example 2.

EXAMPLE 8

This Example describes the labelling of the compound of Example 6 with a non-radioactive rhenium 185,187 isotope to confirm the composition of the final composition.

The composition of the Re-complexes were confirmed by mass spectra (m/e 952 (M+1)).

EXAMPLE 9

This Example describes Platelet Aggregation Inhibition Assays of the compound of Example 8 to illustrate that the compound binds to GPIIb/IIIa receptors when radiolabelled following the procedure of Example 4.

Results: $IC_{50}$: $1.8 \times 10^{-7}$ M

EXAMPLE 10

This study was designed to evaluate the biodistribution pattern of the compound of Example 7 to determine the clearance profile from blood, route of excretion and in vivo stability of the complex by HPLC analysis of urine samples, in a rat model.

The compound of Example 7 was injected (25 mL, 1.5–3.5 mCi/mL) into Sprague-Dawley rats. Groups of three animals were sacrificed at the time points indicated below to determine the amount of radioactivity (%ID/g) remaining in the organs.

| Organ | 5 min | 30 min | 60 min | 120 min |
|---|---|---|---|---|
| Blood | 0.397 | 0.099 | 0.057 | 0.022 |
| Liver | 1.668 | 0.902 | 0.734 | 0.450 |
| Kidney | 4.613 | 1.713 | 0.978 | 0.983 |

EXAMPLE 11

This Example describes the stepwise preparation of the composition having the structure

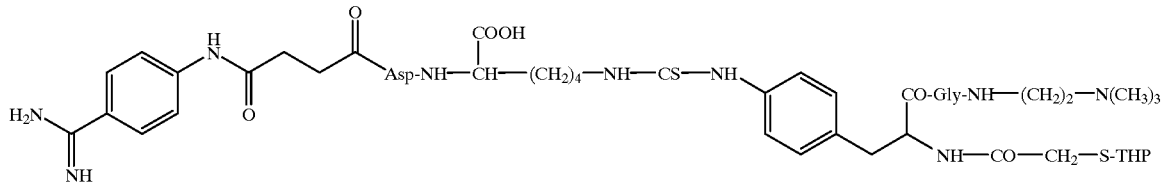

Step a

N-Hydroxysuccinimide ester of N-α-Boc-p-Fmoc-amino-L-Phe

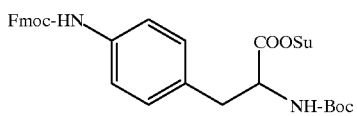

N-α-Boc-p-Fmoc-amino-L-Phe (10.0 g, 19.9 mmol) and N-hydroxysuccinimide (2.52 g, 21.9 mmol) were dissolved in dichloromethane (315 mL). Dicyclohexylcarbodiimide (4.93 g, 23.9 mmol) was subsequently added, and the reaction was stirred overnight at ambient temperature. The dicyclohexylurea was removed by filtration, and the filtrate was diluted with dichloromethane. The organic layer was then extracted with saturated sodium bicarbonate (3x) and washed with brine before drying over anhydrous magnesium sulfate. Filtration and evaporation of the solvent under reduced pressure revealed a white foam (quantitative yield) which was used immediately without further purification. $^1H$ NMR ($CDCl_3$) δ7.75 (d, J=7.6 Hz, 2H, aromatic), 7.59 (d, J=7.3 Hz, 2H, aromatic), 7.39 (t, 2H, aromatic), 7.29 (t, 2H, aromatic), 7.19 (d, J=8 Hz, 1H, carbamate NH), 6.85 (s, 1H, carbamate NH), 4.91 (m, 1H, α-H), 4.49 (d, J=6.7 Hz, 2H, Fmoc $CH_2$), 4.24 (t, 1H, Fmoc CH), 3.17 (m, 2H, $CH_2$-Ar), 2.78 (s, 4H, succinimide $CH_2$'s), 1.39 (s, 9H, OC(CH3)3); $^{13}C$ NMR ($CDCl_3$) δ169, 168, 155, 154, 144, 142, 137, 131, 130, 128, 127, 125, 120, 119, 80.5, 66.8, 46.9, 37.2, 34,7, 28.0, 25.3.

Step b
N-α-Boc-p-Fmoc-amino-L-Phe-Gly-dmen

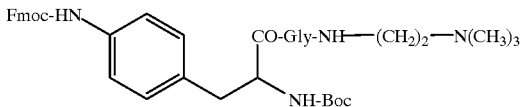

Gly-dmen hydrochloride (2.98 g, 16.4 mmol) was dissolved in a mixture of 1 N sodium bicarbonate (45 mL) and dioxane (45 mL). The N-hydroxysuccinimide ester of N-a-Boc-p-Fmoc-amino-L-Phe (10.8 g, 18.0 mmol) in dioxane (45 mL) was subsequently added, and the reaction was stirred overnight at ambient temperature. The dioxane was then removed under reduced pressure. The product was extracted into ethyl acetate, and the combined organic layer was extracted with saturated sodium bicarbonate (3x) and washed with brine before drying over anhydrous magnesium sulfate. Filtration and evaporation of the solvent under reduced pressure revealed a white solid (7.1 g, 69% yield) which was used without further purification. $^1$H NMR (CDCl$_3$) δ7.85 (br m, 1H, amide NH), 7.73 (d, 2H, aromatic), 7.58 (d, 2H, aromatic), 7.43 (br m, 1H, amide NH), 7.02–7.39 (m, 8H, aromatic), 5.62 (br s, 1H, carbamate NH), 2.44 (m, 2H, Gly CH$_2$), 4.34 (m, 1H, α-H), 4.21 (t, 1H, Fmoc CH), 3.99 (d, 2H Fmoc CH$_2$), 3.57 (m, 2H, CH$_2$N), 2.94 (m, 2H, CH$_2$-Ar), 2.58–2.65 (m, 2H CH$_2$N), 2.40 (s, 6H, N(CH$_3$)$_2$), 1.35 (s, 9H, OC(CH$_3$)$_3$).

Step c
p-Fmoc-amino-L-Phe-Gly-dmen

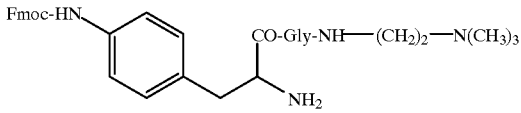

N-α-Boc-p-Fmoc-amino-L-Phe-Gly-dmen (5.00 g, 7.94 mmol) was dissolved in 1:1 TFA/dichloromethane (50 mL each) at 0° C. After the addition was complete, the ice bath was removed, and the reaction was stirred at ambient temperature for 3 hours before removing the solvent under reduced pressure. The residue was purified by reverse phase C$_{18}$ chromatography utilizing a 30% acetonitrile/3% acetic acid/water mobile phase to provide 4.1 g of a clear oil (80% yield). $^1$H NMR (DMSO-d$_6$) δ9.77 (s, 1H, carbamate NH), 8.83 (t, 1H, amide NH), 8.31 (t, 1H, amide NH), 8.19 (br s, 2H, NH$_2$), 7.90 (d, 2H, aromatic), 7.78 (d, 2H, aromatic), 7.39 (m, 6H, aromatic), 7.19 (d, 2H, aromatic), 4.45 (d, 2H, Fmoc CH$_2$), 4.32 (t, 1H, Fmoc CH$_2$), 4.03 (m, 1H, α-H), 3.79 (d, 2H, Gly CH$_2$), 3.42 (q, 2H, NCH$_2$), 3.18 (t, 2H, CH$_2$N), 2.99 (dd, 2H, b-CH$_2$), 2.81 (s, 6H, N(CH$_3$)$_2$), 1.98 (s, 6H, 2 AcOH); $^{13}$C NMR (DMSO-d$_6$) δ172, 170, 169, 154, 144, 141, 138, 132, 130, 128, 127, 125, 120, 118, 81.2, 65.6, 63.6, 58.0, 46.6, 45.0, 36.6, 30.6, 25.0, 20.9.

Step d
S-Tetrahydropyranyl-mercaptoacetyl-p-Fmoc-amino-L-Phe-Gly-dmen

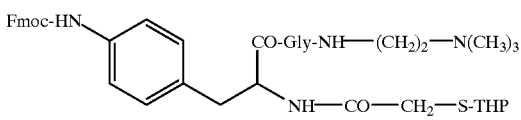

The diacetate salt of p-Fmoc-amino-L-Phe-Gly-dmen (4.00 g, 6.17 mmol) was dissolved in dioxane (20 mL) and 1 N sodium bicarbonate (20 mL). The N-hydroxysuccinimide ester of S-tetrahydropyranyl-mercaptoacetic acid (1.85 g, 6.78 mmol) in dioxane (20 mL) was subsequently added, and the reaction was stirred overnight at ambient temperature before concentrating under reduced pressure. The product was extracted from the remaining aqueous mixture with ethyl acetate (3x). The combined organic layer was washed with saturated sodium bicarbonate (3x), water (1x), and brine (1x) before drying over anhydrous magnesium sulfate. Filtration and evaporation of the solvent under reduced pressure revealed a yellow solid. The crude material (2.20 g, 52% yield) was used immediately without further purification. $^1$H NMR (DMSO-d$_6$) δ9.64 (s, 1H, carbamate NH), 8.38 (d, 1H, amide NH), 8.19 (m, 1H, amide NH), 7.91 (d, 2H, aromatic), 7.68 (d, 2H, aromatic), 7.62 (t, 1H, amide NH), 7.39 (m, 6H, aromatic), 7.18 (d, 2H, aromatic), 4.59 (m, 1H, SCHO), 4.43, d, 2H, Fmoc CH$_2$), 4,36 (t, 1H, Fmoc CH), 3.82 (m, 1H, a-H), 3.18–3.68 (m, 8H, Gly CH$_2$+CONHCH$_2$+OCH$_2$+COCH$_2$S), 2.99 (dd, 1H, b-H of Phe), 2.68 (m, 1H, b-H of Phe), 2.32 (t, 2H, CH$_2$NMe$_2$), 2.18 (s, 6H, N(CH$_3$)$_2$), 1.40–1.80 (m, 6H, 3 CH$_2$'s).

Step e
S-Tetrahydropyranyl-mercaptoacetyl-p-amino-L-Phe-Gly-dmen

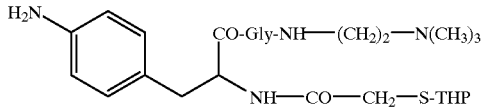

S-Tetrahydropyranyl-mercaptoacetyl-p-Fmoc-amino-L-Phe-Gly-dmen (2.09 g, 3.04 mmol) was dissolved in DMF (30 mL) afterwhich morpholine (6 mL) was added. Due to lack of time, the reaction was stirred overnight at ambient temperature before removing the solvent under reduced pressure. The residue was purified by reverse phase C$_{18}$ column using 30% acetonitrile/2% acetic acid/water to provide 1.1 g of a clear oil (62% yield). $^1$HNMR (CDCl$_3$) δ8.02 (s, 1H, OH),, 7.86 (m, 1H, amide NH), 7.72 (m, 1H, amide NH), 7.61 (m, 1H, amide NH), 6.96 (d, J=8.1 Hz, 2H, aromatic), 6.57 (d, J=8.1 Hz, 2H, aromatic), 6.12 (br s, 2H, NH$_2$), 4.71 (m, 1H, SCHO), 4.53 (m, 1H, a-H), 4.40 (m, 2H, Gly CH$_2$), 2.82–3.89 (m's, 10H, SCH$_2$CO, OCH$_2$, CH$_2$NHCO, CH$_2$N, CH$_2$Ar), 2.64 (s, 6H, N(CH$_3$)$_2$), 1.96 (s, 6H, 2 AcOH), 1.50–1.77 (m, 6H, 3 CH$_2$'s); $^{13}$C NMR (CDCl$_3$) δ177, 172, 171, 170, 161, 146, 130, 126, 116, 82.8, 67.1, 66.3, 65.2, 56.7, 55.8, 45.7, 43.2, 40.5, 36.5, 34.6, 30.8, 25.0, 21.7.

Step f
Fmoc-L-Asp(β-t-Bu)-L-Lys(ε-Boc)-OtBu

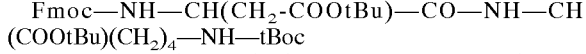

Fmoc—NH—CH(CH$_2$-COOtBu)—CO—NH—CH(COOtBu)(CH$_2$)$_4$—NH—tBoc

Fmoc-L-Asp(β-t-Bu) (10.0 g, 24.3 mmol) and N-hydroxybenzotriazole (4.93 g, 36.4 mmol) were dissolved in DMF (190 mL). The solution was cooled in an ice bath at 0° C. afterwhich EDCHCl (5.12 g, 26.7 mmol) was added. Stirring was continued at 0° C. for one hour before adding a mixture of L-Lys(ε-Boc)-OtBu hydrochloride (8.23 g, 24.3 mmol) and N-methylmorpholine (4.67 g, 46.2 mmol) in DMF (50 mL) dropwise. After the addition was complete, the reaction was stirred overnight at ambient temperature. The reaction mixture was poured into saturated sodium bicarbonate, and the product was extracted into ethyl acetate. The combined organic layer was extracted with saturated sodium bicarbonate (2x), 1 N HCl (2x), and brine (1x) before drying over anhydrous magnesium sulfate. Filtration and evaporation of the solvent under reduced pressure revealed a yellow foam. The material was purified on SiO$_2$ using a methanol/dichloromethane mobile phase to provide 7 grams of a white foam (44% yield). $^1$H NMR (CDCl$_3$) δ7.78 (d, 2H, aromatic), 7.59 (d, 2H, aromatic), 7.38 (t, 2H, aromatic), 7.29 (t, 2H, aromatic), 7.10 (m, 2H, 2 NH), 5.98 (m, 1H, carbamate NH), 4.63 (m, 1H, a-H), 4.57 (m, 1H, α-H), 4.41 (d, 2H, Fmoc CH$_2$), 4.22 (t, 1H, Fmoc CH), 3.33 (m, 2H, CH$_2$N), 2.93 (dd, 1H, β-H of Asp), 2.61 (dd, 1H, b-H of Asp), 1.20–1.84 (m, 6H, 3 CH$_2$'s), 1.44 (3 s's, 27H, 3 OC(CH$_3$)$_3$).

Step g

L-Asp(b-t-Bu)-L-Lys(e-Boc)-OtBu

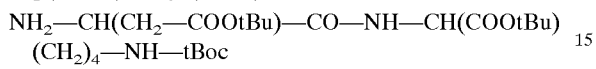

NH$_2$—CH(CH$_2$—COOtBu)—CO—NH—CH(COOtBu)(CH$_2$)$_4$—NH—tBoc

Fmoc-L-Asp(β-t-Bu)-L-Lys(ε-Boc)-OtBu (2.69 g, 3.87 mmol) was dissolved in DMP (38.7 mL) afterwhich morpholine (7.74 mL0 was added. Due to lack of time, the reaction was stirred overnight before removing the solvent under reduced pressure. The residue was purified by reverse phase C$_{18}$ chromatography using 30% ethanol/3% acetic acid/water as the eluent to provide 1.3 g of a clear oil (63 % yield). $^1$H NMR (CDCl$_3$) δ7.80 (d, 1H, amide NH), 5.58 (br s, 2H, NH2), 4.81 (m, 1H, carbamate NH), 4.39 (m, 1H, a-H), 3.79 (m, 1H, a-H), 3.05 (m, 2H, CH$_2$N), 2.78 (dd, 1H, b-H of Asp), 2.59 (dd, 1H, b-H of Asp), 1.42 (3 s's, 27H, 3 OC(CH$_3$)$_3$), 1.25–1.82 (m, 6H, 3 CH$_2$'s); $^{13}$C NMR (CDCl$_3$) δ177, 173, 172, 171, 82.0, 81.6, 79.1, 52.3, 51.4, 40.0, 39.4, 31.8, 29.0, 28.2, 27.8, 27.7, 22.0,20.8.

Step h

ABAS-L-Asp(β-t-Bu)-L-Lys(ε-Boc)-OtBu

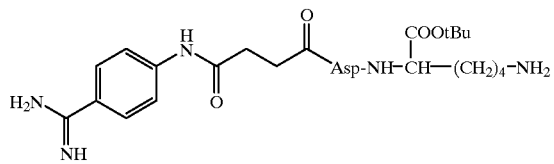

ABAS hydrochloride (0.64 g, 2.4 mmol) was dissolved in DMF(30 mL). N-methylmorpholine (0.24 g, 2.4 mmol) and isobutyl chloroformate (0.32 g, 2.4 mmol) were added after cooling to 0° C. After stirring for 0.5 hour, L-Asp(β-t-Bu)-L-Lys(ε-Boc)-OtBu AcOH (1.2 g, 2.3 mmol) and N-methylmorpholine (0.23 g, 2.3 mmol) were added in DMF (15 mL). The reaction was then stirred overnight at ambient temperature before removing the solvent under reduced pressure. The residue was purified by reverse phase C$_{18}$ chromatography using 30% acetonitrile/2% acetic acid/water as the eluent to provide a white foam (1.3 g, 76% yield). $^1$H NMR (CDCl$_3$) δ10.3 (br s, 1H, amidine NH), 8.72 (br s, 1H, Ar-NH), 7.98 (d, 1H, amide NH), 7.66 (m, 4H, aromatic), 7.57 (br d, 1H, amide NH), 5.04 (t, 1H, carbamate NH), 4.81 (m, 1H, a-H), 4.28 (m, 1H, a-H), 2.99 (m, 2H, CH$_2$NH), 2.79 (m, 4H, COCH$_2$CH$_2$CO), 2.59 (m, 2H, b-H's of Asp), 2.01 (s, 3H, AcOH), 1.10–1.80 (m, 6H, 3 CH$_2$'s), 1.39 (3 s's, 27H, 3 OC(CH$_3$)$_3$).

Step i

ABAS-L-Asp-L-Lys2TFA

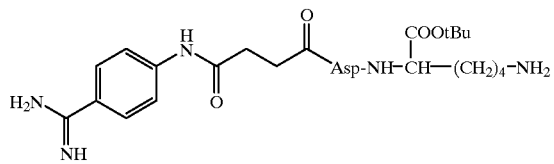

ABAS-L-Asp(β-t-Bu)-L-Lys(ε-Boc)-OtBu (1.25 g, 1.66 mmol) was dissolved in 1:1 TFA/dichloromethane (10 mL each). The reaction was stirred overnight at ambient temperature before removing the solvent under reduced pressure to reveal a yellow powder (0.96 g, 82%) which was used without further purification. $^1$H NMR (D$_2$O) δ7.78 (d, 2H, aromatic), 7.62 (d, 2H, aromatic), 4.72 (m, 1H, a-H), 4.38 (m, 1H, a-H), 2.89 (m, 4H, COCH$_2$CH$_2$CO), 2.69 (m, 4H, CH$_2$N+2 b-H's of Asp), 1.25–1.89 (m, 6H, 3 CH$_2$'s).

Step j

ABAS-L-Asp-L-Lys p-amino-Phe(α-S-THP-mercaptoacetyl)-Gly-dmen Thiourea

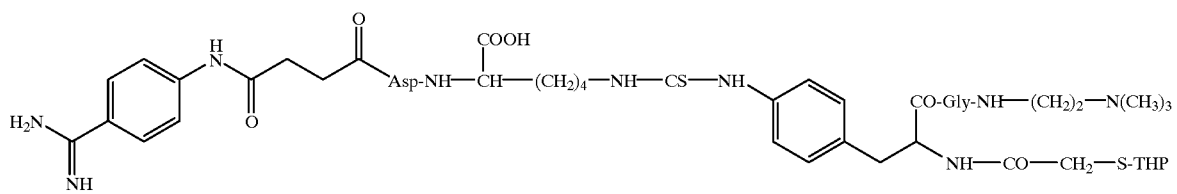

The diacetate salt of S-tetrahydropyranyl-mercaptoacetyl-p-amino-L-Phe-Gly-dmen (260 mg, 0.44 mmol) was dissolved in DMF (4 mL) in the presence of N-methylmorpholine (90 mg, 0.89 mmol, 98 ml). Thiocarbonyldiimidazole (83 mg, 0.47 mmol) was subsequently added. After stirring for 3 hours, ABAS-L-Asp-L-Lys-2TFA (310 mg, 0.44 mmol) was added in DMF (4 mL) followed by additional N-methylmorpholine (222 mg, 2.20 mmol, 242 ml). The reaction was stirred overnight at ambient temperature before removing the solvent under reduced pressure. The material was initially flash chromatographed on C$_{18}$ using an isocratic 30% acetonitrile//2% acetic acid/water mobile phase. This rapid elution resulted in the separation of unreacted starting materials from the desired product (R$_f$=0.23, 30% acetonitrile/3% acetic acid/water)

and the symmetrical thiourea side product. The target compound was finally cleanly isolated by HPLC using a Nova-Pak $C_{18}$ 30×300 mm column to provide 40 mg of a glassy solid (10% yield). Mobile Phase A: 0.1% TFA/water; Mobile Phase B: 0.1%TFA/10%water/acetonitrile; Gradient: 90%A/ 10%B to 60% A/40% B over 15 minutes holding at 60% A/40% B for 15 minutes; Retention Time: 19 minutes; Mass Spec. (ESI) 986 (M+1, 10%), 493 ((M+2)/2, 100%).

EXAMPLE 12

The compound of Example 11 was radiolabeled with Tc-99m according to method A described in Example 2.

EXAMPLE 13

This Example describes the labelling of the compound of Example 11 with a non-radioactive rhenium 185,187 isotope to confirm the composition of the final composition.

The composition of the Re-complexes were confirmed by mass spectra (m/e 1102 (M+1).

EXAMPLE 14

This Example describes Platelet Aggregation Inhibition Assays of the compound of Example 13 to illustrate that the compound binds to GPIIb/IIIa receptors when radiolabelled following the procedure of Example 4.

$IC_{50}$:4.6×10$^{-8}$M

EXAMPLE 15

This study was designed to evaluate the biodistribution pattern of the compound of Example 12 to determine the clearance profile from blood, route of excretion and in vivo stability of the complex by HPLC analysis of urine samples, in a rat model.

The compound of Example 12 was injected into Sprague-Dawley rats according to the procedure outlined in Example 5. The amount of radioactivity present in the major excretionary organs at different time points (1, 4 and 24 hours) are given below.

| | All values are % ID/g | | |
|---|---|---|---|
| Organ | 1 hour | 4 hours | 24 hours |
| Blood | 0.118 | 0.062 | 0.010 |
| Liver | 0.187 | 0.096 | 0.044 |
| Kidney | 1.620 | 1.434 | 1.066 |
| Sml. Int & Contents | 0.448 | 0.087 | 0.008 |
| % ID excreted in the urine at 24 hr. | | | 49.95 |
| % ID excreted in the feces at 24 hr. | | | 43.80 |

EXAMPLE 16

Canine Model for Pulmonary Embolism

These studies are designed to serve as a preliminary screen of various radiolabeled pharmaceuticals for the purpose of imaging pulmonary emboli (PE) and/or deep vein thrombus (DVT).

Procedure: The dog is first anesthetized with an intravenous injection of sodium pentobarbital (30 mg/kg). An IV catheter is placed into the jugular vein and advanced to the pulmonary artery. Visualization of the catheter placement is facilitated using fluoroscopy. Embolization coils of various sizes (3–8 mm) are next released via the catheter using the appropriate guide wire, and localization of the coils is followed by fluoroscopy. After a satisfactory number of coils (3–5) have been placed and visualized, the catheter is removed and the vein ligated. The formation of a deep vein thrombus (DVT) in the saphenous vein is facilitated by the placement of a 16 gauge needle into the vein followed by the passage of a 5 mm embolization coil through the needle directly into the vein.

IV injection (cephalic vein) of the radiolabeled test article occurs approximately 30–45 minutes post placement of the embolization coils. Approximate activity injected is 2.5–3.5mCi. Beginning at 30 minutes post injection and continuing for several hours at 30 minute intervals, the animal is scintigraphed in both the lateral and supine positions.

At the conclusion of the imaging portion of the study (3 hours) the animal is sacrificed, and selected tissues removed for scintillation counting. The coils are located, removed and quantitated for uptake of the radiotracer. From these values is determined the target:non-target ratios and blood clearance of the test article.

| Sample | Clot/blood | % ID/g |
|---|---|---|
| Blood | — | 0.001 |
| Clot 1 (DVT) | 320 | 0.29 |
| Clot 2 (PE) | 38 | 0.03 |
| Clot 3 (PE) | 33 | 0.03 |
| Clot 4 (PE) | 30 | 0.03 |
| Clot 5 (PE) | 57 | 0.05 |

EXAMPLE 17

This Example describes the stepwise preparation of the composition having the structure

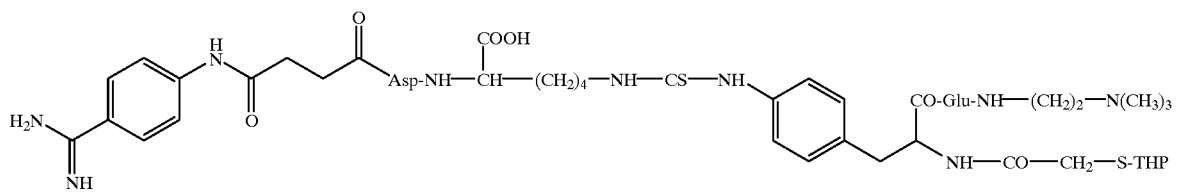

ABAS-L-Asp-L-Lys-p-amino-Phe(α-S-THP-mercaptoacetyl)-Glu-dmen Thiourea

Step a

ABAS-L-Asp-L-Lys-p-amino-Phe(α-S-THP-mercaptoacetyl)-Glu-dmen Thiourea (MP-2068) was prepared in a manner similar to ABAS-L-Asp-L-Lys-p-amino-Phe(a-S-THP-mercaptoacetyl)-Glu-dmen Thiourea (see example 3) except that Glu(g-t-Bu)-dmen was substituted for Gly-dmen.

EXAMPLE 18

This Example describes the stepwise preparation of the composition having the structure

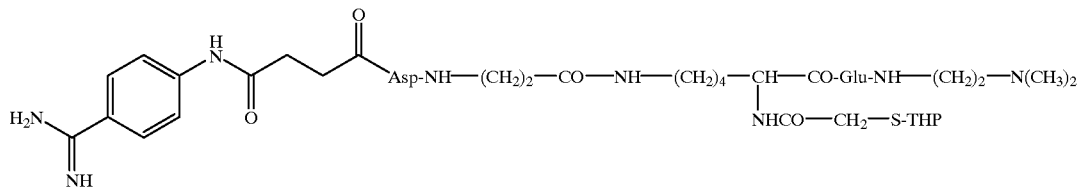

before concentrating under reduced pressure. The remaining aqueous layer was acidified with 1 N HCl, and the product was extracted into ethyl acetate (3x). The combined organic layer was washed with brine and dried over anhydrous magnesium sulfate. Filtration and evaporation of the solvent under reduced pressure revealed an off-white foam (5.68 g, 40% yield). The crude foam (5.62 g, 12.4 mmol), N-hydroxysuccinimide (1.58 g, 13.7 mmol), and dicyclohexylcarbodiimide (3.0 g, 14.9 mmol) were dissolved in dichloromethane (110 mL). The reaction was continued overnight before filtering to remove the dicyclohexylurea. The filtrate was diluted with dichloromethane and extracted with saturated sodium bicarbonate (3x) before washing with brine. The solution was dried over anhydrous magnesium sulfate, filtered, and evaporated to reveal an off-white foam (6.2 g, 91% yield). This material was used without further purification.

Step a
N-Hydroxysuccinimide Ester of Cbz-β-Ala

N-Carbobenzyloxy-β-Ala (15.0 g, 67.2 mmol), N-hydroxysuccinimide (8.5 g, 73.9 mmol), and dicyclohexylcarbodiimide (16.6 g, 80.6 mmol) were dissolved in dichloromethane (600 mL). The reaction was continued overnight before filtering to remove the dicylohexylurea. The filtrate was then diluted with dichloromethane and extracted with saturated sodium bicarbonate (3x) and washed with brine before drying over anhydrous magnesium sulfate. Filtration and evaporation of the solvent under reduced pressure revealed a clear oil (20.9 g, 97% yield).

The material was used immediately without further purification.

Step b

N-Carbobenzoxy-β-Alanyl-(α-Boc)-lysyl-succinimidate ester

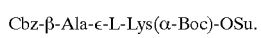

The α-Boc-L-Lys (10.0 g, 31.2 mmol) was dissolved in water (85 mL) in the presence of sodium bicarbonate (2.62 g, 31.2 mmol). The N-hydroxysuccinimide ester of Z-β-Ala (7.68 g, 31.2 mmol) in acetonitrile (85 mL) was subsequently added, and the reaction was continued overnight Step c Ala-ε-L-Lys(α-Boc)-Glu(γ-t-Bu)-dmen

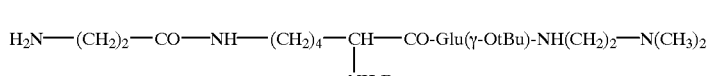

Cbz-β-Ala-ε-L-Lys(α-Boc)-OSu (3.0 g, 5.47 mmol) and Glu(γ-t-Bu)-dmen (1.42 g, 5.21 mmol) were dissolved in dichloromethane (60 mL), and the reaction was continued overnight. It was diluted with dichloromethane and extracted with saturated sodium bicarbonate(3x) and washed with brine before drying over anhydrous magnesium sulfate. Filtration and evaporation of the solvent under reduced pressure revealed a white foam which was purified by reverse phase C$_{18}$ chromatography using an acetonitrile/acetic acid/H$_2$O gradient (2.50 g, 68% yield). The material (2.25 g, 3.19 mmol) was dissolved in methanol (25 mL). After flushing with nitrogen, the catalyst was added, and the hydrogenolysis was performed in the usual manner. After five hours, the reaction was filtered through Celite, and the filtrate was concentrated to reveal a quantitative yield of a white foam.

Step d

ABAS-L-Asp-β-Ala-ε-L-Lys(α-S-THP-mercaptoacetyl)-Glu-dmen

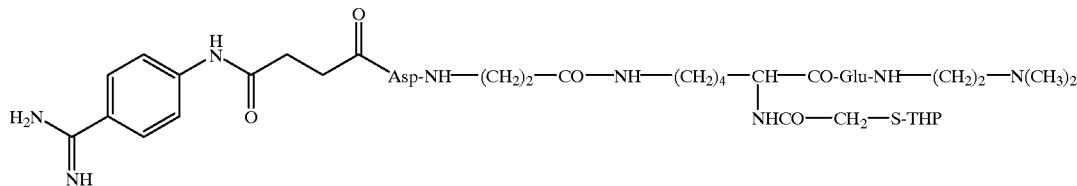

The ABAS-Asp(β-t-Bu) (1.30 g, 2.79 mmol) was dissolved in DMF (70 mL) at 0° C. N-methylmorpholine (0.28 g, 0.31 mL, 2.79 mmol) and isobutyl chloroformate (0.38 g, 0.36 mL, 2.79 mmol) were subsequently added. After stirring for 0.5 hour at 0° C., a solution of Ala-e-L-Lys(a-Boc)-Glu(g-t-Bu)-dmen (1.6 g, 2.79 mmol) in DMF (30 mL) was added. The reaction was gradually permitted to warm to room temperature for overnight stirring. The solvent was then removed under reduced pressure. The crude material was purified by reverse phase $C_{18}$ chromatography using an acetonitrile/acetic acid/water gradient to afford a white solid (500 mg, 17% yield, not accounting for the unreacted ABAS-Asp(β-tBu)). This material was then dissolved in 1:1 TFA/dichloromethane (10 mL), and the deprotection was continued overnight before removing the solvent under reduced pressure. The residue was dissolved in water and filtered through $C_{18}$ to give a clear oil (390 mg, 86% yield). This deprotected peptide was finally dissolved in water (5 mL) in the presence of sodium bicarbonate (194 mg, 2.31 mmol). The N-hydroxysuccinimide ester of S-tetrahydropyranyl-mercaptoacetic acid (115 mg, 0.42 mmol) in acetonitrile (5 mL) was subsequently added, and the reaction was continued overnight. The reaction was concentrated under reduced pressure, and the remaining aqueous layer was acidified with 1 N HCl to pH 3. The material was then loaded onto a flash $C_{18}$ column for removal of the bulk impurities followed by HPLC purification using an acetonitrile/water/0.1% TFA mobile phase system. After lyophilization, approximately 60 mg were obtained.

EXAMPLE 19

The compound of Example 18 was radiolabeled with Tc-99m according to method A and B described in Example 2.

EXAMPLE 20

This Example describes the labelling of the compound of Example 11 with a non-radioactive rhenium 185,187 isotope to confirm the composition of the final composition.

The composition of the Re-complexes were confirmed by mass spectra (m/e 1013 (M+1)).

EXAMPLE 21

This Example describes Platelet Aggregation Inhibition Assays of the compound of Examples 18 and 20 to illustrate that the compound binds to GPIIb/IIIa receptors when radiolabelled following the procedure of Example 4.

Results: $IC_{50}$:$4.9 \times 10^{-7}$M (Example 18) and $4.1 \times 10^{-7}$M (Example 20)

EXAMPLE 22

This study was designed to evaluate the biodistribution pattern of the compound of Example 19 to determine the clearance profile from blood, route of excretion and in vivo stability of the complex by HPLC analysis of urine samples, in a rat model.

The compound of Example 19 was injected into Sprageue-Dawley rats according to the procedure outlined earlier. The amount of radioactivity present in the major excretionary organs at different time points (1, 4 and 24 hours) are given below.

| | All values are % ID/g | | |
|---|---|---|---|
| Organ | 1 hour | 4 hours | 24 hours |
| Blood | 0.067 | 0.011 | 0.004 |
| Liver | 0.158 | 0.024 | 0.009 |
| Kidney | 0.864 | 0.520 | 0.241 |
| Sml. Int & Contents | 0.645 | 0.015 | 0.002 |
| % ID excreted in the urine at 24 hr. | | | 41.217 |
| % ID excreted in the feces at 24 hr. | | | 32.758 |

EXAMPLE 23

The compound of claim 19 was administered to a canine according to the general protocol described in Example 16. The following results were obtained.

| Sample | Clot/blood | % ID/g |
|---|---|---|
| Blood | — | 0.0018 |
| Clot 1 (DVT) | 43 | 0.0828 |
| Clot 2 (PE) | 6 | 0.0114 |
| Clot 3 (PE) | 65 | 0.125 |
| Clot 4 (PE) | 74 | 0.142 |
| Clot 5 (PE) | 64 | 0.1232 |

EXAMPLE 24

This Example describes the stepwise preparation of a compound having the structure

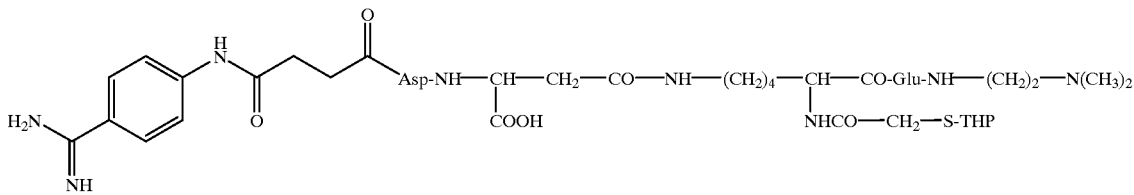

Step a
ABAS-L-Asp-L-Asp-β,ε-Lys(α-S-THP-mercaptoacetyl)-
Glu-dmen

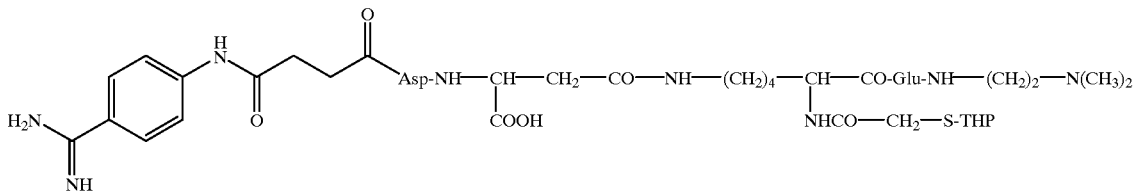

ABAS-L-Asp-L-Asp-β,ε-Lys(α-S-THP-mercaptoacetyl)-Glu-dmen was prepared in a manner similar to Example 18 (as previously desribed) except that Cbz-L-Asp(β-OSu)-OBn was substituted for Cbz-β-Ala-OSu. Mass Spec. (ESI) 950 (M+1, 10%), 476.5 (M+2)/2, 100%); Retention Time: 22 min. (0.46×25 cm Vydac $C_{18}$, 1 mL/min flow rate); Gradient: 95% A–70% A over 35 minutes (Solvent A: 0.1% TFA/water, Solvent B: 0.1% TFA/10% water/acetonitrile).

EXAMPLE 25

This Example describes the stepwise preparation of a compound having the structure

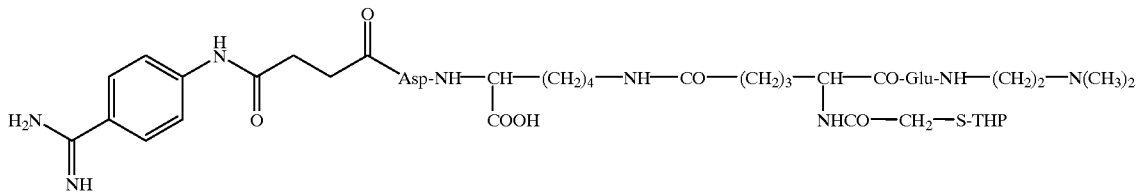

Step a
S-THP-mercaptoacetyl-AAA(δ-OBn)-Glu(γ-t-Bu)-dmen

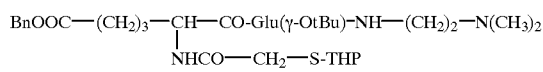

S-THP-mercaptoacetyl-aminoadipic acid (S-THP-MA-AAA, 3.16 g, 7.72 mmol) and N-hydroxysuccinimide (0.98 g, 8.49 mmol) were dissolved in anhydrous dichloromethane (118 mL). Dicyclohexylcarbodiimide (1.75 g, 8.49 mmol) was subsequently added, and the reaction was continued overnight at ambient temperature before removing the dicyclohexylurea by filtration. The filtrate was evaporated to dryness, and the residue was immediately dissolved in 1:1 acetonitrile/water (20 mL each) along with Glu(γ-t-Bu)-dmen (2.53 g, 9.26 mmol) in the presence of sodium bicarbonate (0.78 g, 9.26 mmol). The reaction was continued overnight at room temperature. The solvent was finally removed under reduced pressure, and the crude material was dissolved in 30% acetonitrile/2% acetic acid/water in the presence of 0.4 mL of acetic acid. It was loaded onto a reverse phase $C_{18}$ column packed with the same solvent system. Isocratic elution with 30% acetonitrile/2% acetic acid/water afforded (2.70 g, 48% yield). $R_f$=0.12 (30% acetonitrile/2% acetic acid/water).

Step b
S-THP-mercaptoacetyl-AAA-Glu(γ-t-Bu)-dmen

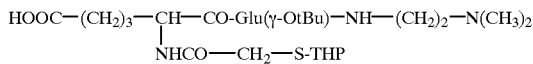

S-THP-mercaptoacetyl-AAA(δ-OBn)-Glu(g-t-Bu)-dmen.AcOH (1.93 g, 2.66 mmol) was dissolved in acetonitrile (95 mL) and water (50 mL). One equivalent of 1 N sodium hydroxide (2.6 mL) was subsequently added dropwise. After 10 minutes, another equivalent of 1 N sodium hydroxide was added. The reaction was then continued overnight at room temperature before adjusting the pH to 7 with 1 N hydrochloric acid (2 mL). The solvent was removed under reduced pressure, and the residue was dissolved in 20% acetonitrile/water and loaded onto a reverse phase $C_{18}$ column packed with 10% acetonitrile/water. Isocratic elution with 20% acetonitrile/water ultimately gave 920 mg of a white powder (60% yield). $R_f$=0.57 (60% acetonitrile/water).

Step c

S-THP-mercaptoacetyl-AAA(δ-OSu)-Glu(γ-t-Bu)-dmen

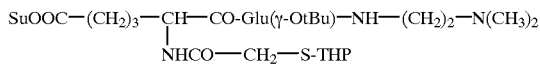

S-THP-mercaptoacetyl-AAA-Glu(γ-t-Bu)-dmen (400 mg, 0.70 mmol) and N-hydroxysuccinimide (88 mg, 0.77 mmol) were dissolved in anhydrous dichloromethane (11 mL). Dicyclohexylcarbodiimide (170 mg, 0.84 mmol) was subsequently added, and the reaction was continued overnight at ambient temperature. The dicyclohexylurea was removed by filtration, and the filtrate was diluted with dichloromethane. The organic layer was extracted with saturated sodium bicarbonate (3x) and washed with brine (1x) before drying over anhydrous magnesium sulfate. Filtration and evaporation of the solvent under reduced pressure revealed a white foam hich was used without purification.

Step d

ABAS-L-Asp-L-Lys(ε-AAA(N-α-S-THP-mercaptoacetyl)-Glu(γ-t-Bu)-dmen)

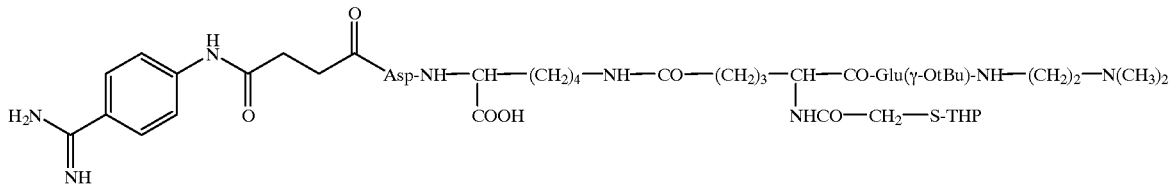

ABAS-L-Asp-L-Lys.2TFA (25.6 mg, 0.034 mmol) and S-THP-mercaptoacetyl-AAA(δ-OSu)-Glu(γ-t-Bu)-dmen (19.5 mg, 0.041 mmol) were dissolved in DMF (0.5 mL) in the presence of triethylamine (0.012 mL). The reaction was continued overnight before diluting with 1:1 acetonitrile/water (2 mL) and acidifying to pH 4 with 0.2 N hydrochloric acid. The solvent was subsequently removed under reduced pressure. The residue was purified by reverse phase $C_{18}$ chromatography using an acetonitrile/water gradient system to afford 16 mg of product (46% yield). $R_f$=0.54 (33% acetonitrile/0.5 N sodium chloride); $^1$H NMR (1:1 $CD_3CN$/$D_2O$, unreferenced) δ8..12 (dd, 4H, aromatic), 5.31 (m, 2H), 5.09 (m, 1H), 4.60 (m, 1H), 4.36 (m, 2H), 3.93 (m, 4H), 3.74 (m, 3H), 3.61 (m, 3H), 3.45 (t, 2M, 3.18 (s+m, 10H), 2.99 (m, 2H), 2.69 (m, 4H), 2.56 (m, 2H), 2.44 (m, 1H), 1.88–2.34 (m, 14H), 1.79 (s, 9H), 1.57–1.83 (m, 4H).

Step e

ABAS-L-Asp-L-Lys(ε-AAA(α-S-THP-mercaptoacetyl)-Glu-dmen)

ABAS-L-Asp-L-Lys(ε-AAA(α-S-THP-mercaptoacetyl)-Glu(γ-t-Bu)-dmen) (16 mg, 0.016 mmol) was dissolved in formic acid (1 mL). The reaction was continued overnight before evaporating the solvent under reduced pressure. The residue was evaporated several times from 1:1 acetonitrile/water to generate 14 mg of sufficiently pure product (91% yield). $^1$H NMR (1:1 $CD_3CN$/$D_2O$, unreferenced) δ8.74 (d, 1H, 3.4 Hz), 8.54 (s, 1H), 8.19 (dd, 8.2, 1.8 Hz, 4H, aromatic), 5.34 (m, 1H), 5.07 (m, 1H), 4.59 (m, 2H), 4.41 (m, 2H), 3.99 (m, 4H), 3.79 (m, 2H), 3.68 (m, 4H), 3.49 (m, 2H), 3.29 (s+m, 8H), 3.11 (m, 6H), 2.78 (m, 4H), 1.62–2.62 (m, 18H).

EXAMPLE 26

The compound of Example 25 was radiolabeled according to the method A described Example 2.

EXAMPLE 27

This Example describes the labelling of the compound of Example 25 with non radioactive rhenium 185,187 isotope to confirm the composition of the final composition.

The composition of the Re-complexes were confirmed by mass spectra (m/e 1096(M+1)).

EXAMPLE 28

This Example describes Platelet Aggregation Inhibition Assays of the compound of Example 26 and 27 to illustrate that the compound binds to GPIIb/IIIa receptors when radiolabelled following the procedure of Example 4.

Results: $2.9 \times 10^{-7}$ M (Example 26) and $2.7 \times 10^{-7}$ (Example 27)

EXAMPLE 29

This study was designed to evaluate the biodistribution pattern of the compound of Example 26 to determine the clearance profile from blood, route of excretion and in vivo stability of the complex by HPLC analysis of urine samples, in a rat model.

The compound of Example 26 was injected (25 mL, 1.5–3.5 mCi/mL) into Sprague-Dawley rats. Groups of three animals were sacrificed at the time points indicated below to determine the amount of radioactivity remaining in the organs.

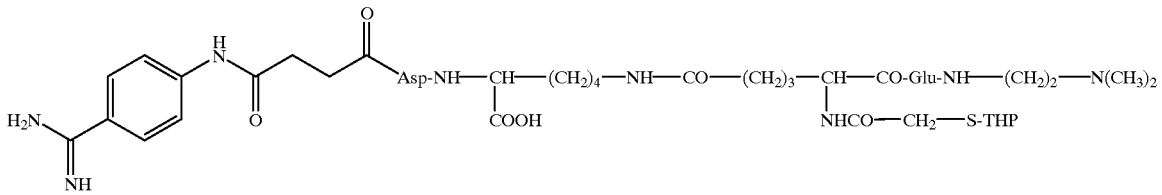

| All values are % ID/g | | | |
|---|---|---|---|
| Organ | 1 hour | 4 hours | 24 hours |
| Blood | 0.067 | 0.011 | 0.007 |
| Liver | 0.043 | 0.015 | 0.014 |
| Kidney | 0.628 | 0.536 | 0.227 |
| Sml. Int & Contents | 0.206 | 0.031 | 0.009 |
| % ID excreted in the urine at 24 hr. | | | 54.708 |
| % ID excreted in the feces at 24 hr. | | | 16.277 |

EXAMPLE 30

This Example describes the stepwise preparation of

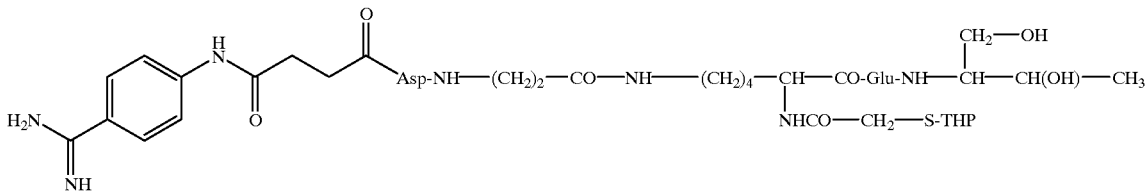

ABAS-L-Asp-β-Ala-ε-Lys(α-S-THP-mercaptoacetyl)-Glu-Thr(ol)

Step a

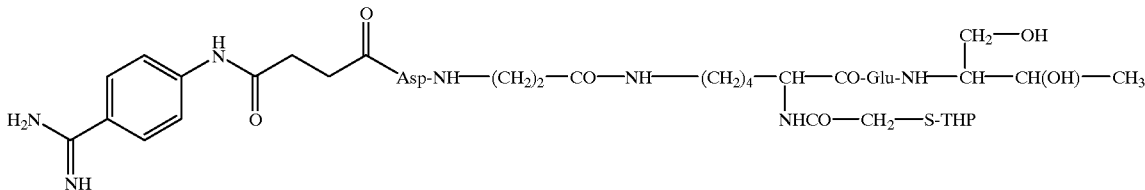

ABAS-L-Asp-β-Ala-ε-Lys(α-S-THP-mercaptoacetyl)-Glu-Thr(ol) was prepared in a manner similar to MP-2065 (as previously desribed) except that threoninol was substituted for dmen. Mass Spec. (ESI) 924 (M+1, 20%), 462.9 ((M+2)/2, 100%); Retention Time: 21 min. (0.46×25 cm Vydac $C_{18}$, 1 mL/min flow rate); Gradient: 100% A–60% A over 30 minutes (Solvent A: 0.1% TFA/water, Solvent B: 0.1% TFA/10% water/acetonitrile).

EXAMPLE 31

This Example describes the stepwise preparation of the compound having the structure Step a
N-Boc-L-Asp(β-OtBu)-L-Lys(ε-Cbz)-OtBu L-Lys(ε-Cbz)-OtBu hydrochloride (7.93 g, 21.2 mmol) was dissolved in dichloromethane (140 mL) in the presence of the triethylamine (2.15 g, 21.2 mmol, 3.0 mL). N-Boc-L-Asp(β-OtBu)-OSu (10.0 g, 21.2 mmol) was subsequently added, and the reaction was continued overnight at ambient temperature before diluting with dichloromethane. The organic layer was extracted with saturated sodium bicarbonate (3x), 1 N hydrochloric acid (2x), and washed with brine (1x) before drying over anhydrous magnesium sulfate. Filtration and evaporation of the solvent under reduced pressure revealed a yellow foam which was purified on $SiO_2$ using dichloromethane as the eluent to provide 7.2 grams of a white foam (56% yield). $^1$H NMR ($CDCl_3$) δ7.28 (m, 5H, aromatic), 7.05 (m, 1H, carbamate NH), 5.64 (d, 1H, amide NH), 5.05 (dd, 2H, benzylic $CH_2$), 5.00 (m, 1H, carbamate NH), 4.41 (m, 2H, 2 a-H's), 3.18 (m, 2H, $CH_2N$), 2.84 (dd, 1H, Asp b-H), 2.58 (dd, 1H, Asp b-H), 1.44 (3 s's, 27H, 3 $OC(CH_3)_3$), 1.20–1.85 (m, 6H, 3 $CH_2$'s).

Step b

N-Boc-L-Asp(β-OtBu)-L-Lys-OtBu

N-Boc-L-Asp(β-OtBu)-L-Lys(ε-Cbz)-OtBu (4.97 g, 8.18 mmol) was dissolved in methanol (85 mL). After flushing with nitrogen, 10% Pd/C catalyst (0.5 g) was added. The mixture was shaken for 6 hours at ambient temperature under an atmosphere of hydrogen (40 p.s.i.). The reaction was filtered through a pad of Celite, and the filtrate was concentrated under reduced pressure to reveal a mauve oil in quantitative yield. $^1$H NMR ($CDCl_3$) δ7.03 (d, 1H, amide NH), 5.74 (d, 2H, amide NH), 4.42 (m, 2H, 2 a-H's), 2.84 (dd, 1H, Asp b-H), 2.62 (m, $CH_2N$+Asp b-H), 1.44 (3 s's,

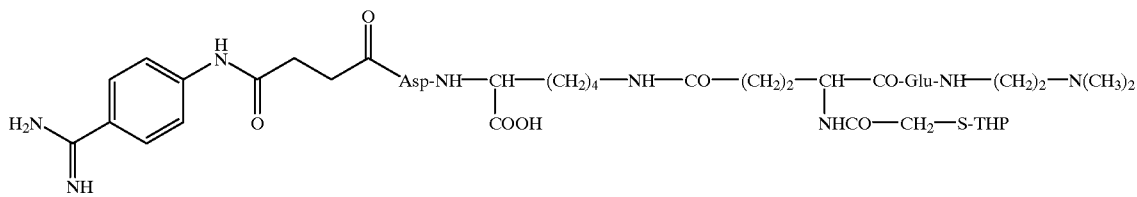

27H, 3 OC(CH$_3$)$_3$), 1.20–1.85 (m, 6H, 3 CH$_2$'s); $^{13}$C NMR (CDCl$_3$) δ172, 171, 170, 156, 81.9, 81.6, 80.2, 52.7, 50.6, 41.6, 37.2, 33.0, 32.1, 28.1, 27.8, 27.7, 21.9.

Step c
N-Boc-L-Asp(β-OtBu)-L-Lys(ε-γ-L-Glu(N-α-Cbz)-OBn)-OtBu

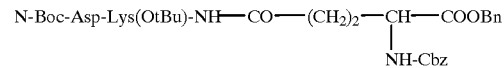

N-Cbz-L-Glu-OBn (2.77 g, 7.45 mmol) and N-hydroxybenzotriazole (1.51 g, 11.2 mmol) were dissolved in DMF (55 mL). The solution was cooled in an ice bath afterwhich EDC.HCl (1.57 g, 8.20 mmol) was added. Stirring was continued at 0° C. for one hour before adding a mixture of N-Boc-L-Asp(b-OtBu)-L-Lys-OtBu (3.78 g, 7.45 mmol) and N-methylmorpholine (0.68 g, 6.70 mmol, 1.0 mL) in DMF (15 mL) dropwise. After the addition was complete, the reaction was permitted to gradually warm to room temperature for overnight stirring. The reaction mixture was poured into saturated sodium bicarbonate, and the aqueous mixture was extracted into ethyl acetate (3x). The combined ethyl acetate layer was washed with saturated sodium bicarbonate (2x), water (2x), 1 N hydrochloric acid (2x), and brine (1x) before drying over anhydrous magnesium sulfate. Filtration and evaporation of the solvent under reduced pressure revealed a yellowish foam (5.8 g, 94% yield). This material appeared sufficiently pure by proton NMR, so no further purification was necessary. $^1$H NMR (CDCl$_3$) δ7.29 (m, 5H, aromatic), 7.04 (d, 1H, carbamate NH), 6.10 (t, 1H, amide NH), 5.91 (d, 1H, amide NH), 5.70 (d, 1H, carbamate NH), 5.07 (s, 2H, benzylic CH$_2$), 4.38 (m, 3H, 3 a-H's), 3.13 (m, 2H, CH$_2$N), 2.82 (dd, 1H, Asp b-H), 2.56 (dd, 1H, Asp b-H), 2.16 (m, 2H, Glu g CH$_2$), 1.39 (3 s's, 27H's, 3 OC(CH$_3$)$_3$), 1.22–1.79 (m, 8H, 4 CH$_2$'s).

Step d
N-Boc-L-Asp(β-OtBu)-L-Lys(ε-γ-L-Glu)

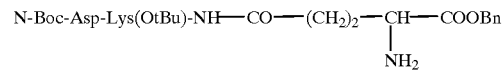

N-Boc-L-Asp(β-OtBu)-L-Lys(ε-γ-L-Glu(N-α-Cbz)-OBn)-OtBu (5.8 g, 7.01 mmol) was dissolved in methanol (75 mL). After flushing with nitrogen, 10% Pd/C catalyst (0.5 g) was added. The mixture was shaken for 6 hours at ambient temperature under an atmosphere of hydrogen (40 p.s.i.). The reaction was filtered through a pad of Celite, and the filtrate was concentrated under reduced pressure to reveal a white foam in quantitative yield. $^1$H NMR (CDCl$_3$) δ7.75 (br d, 1H, amide NH), 7.41 (br d, 1H, amide NH), 6.08 (br d, 1H, carbamate NH), 4.54 (m, 1H, a-H), 4.28 (m, 1H, a-H), 3.61 (m, 1H, a-H), 3.07 (m, 2H, CH$_2$N), 2.67 (m, 2H, NH$_2$), 2.37 (m, 2H, Asp b-H's), 2.31 (m, 2H, Glu g-H's), 1.39 (3 s's, 27H's, 3 OC(CH$_3$)$_3$), 1.19–1.72 (m, 8H, 4 CH$_2$'s); $^{13}$C NMR (CDCl$_3$) d 174, 173, 171.4, 171.3, 171.0, 156, 81.8, 81.4, 79.9, 54.2, 53.5, 50.6, 50.7, 38.8, 38.1, 32.0, 31.9, 28.0, 27.9, 27.8, 22.2.

Step e
N-Boc-L-Asp(β-OtBu)-L-Lys(ε-γ-L-Glu(N-α-S-THP-mercaptoacetyl))-OtBu

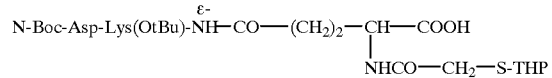

N-Boc-L-Asp(β-OtBu)-L-Lys(ε-γ-L-Glu(N-α-Cbz)-OBn)-OtBu (4.12 g, 6.84 mmol) was suspended in a mixture of 1 N sodium bicarbonate (20 mL) and dioxane (20 mL). The NHS ester of S-TBP-mercaptoacetic acid (1.78 g, 6.51 mmol) was subsequently added, and the reaction was continued overnight at room temperature. The dioxane was removed under reduced pressure, and the remaining aqueous layer was acidified with 1 N hydrochloric acid. The product was then extracted into ethyl acetate (3x), and the combined ethyl acetate layer was washed with 1 N hdrochloric acid (2x), water (2x), and brine (1x) before drying over anhydrous magnesium sulfate. Filtration and evaporation of the solvent under reduced pressure revealed a white foam which was purified on SiO$_2$ using 5% methanol / 2% acetic acid/dichloromethane as an isocratic eluent. Mixed fractions were discarded (2.1 g, 42% isolated yield). R$_f$=0.62 (20% methanol/dichloromethane).

Step f
N-Boc-L-Asp(β-OtBu)-L-Lys(ε-γ-L-Glu(N-α-S-THP-mercaptoacetyl)-Gly-dmen)-OtBu

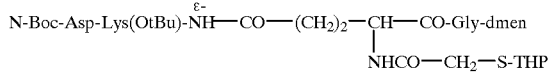

N-Boc-L-Asp(β-OtBu)-L-Lys(ε-γ-L-Glu(N-α-S-THP-mercaptoacetyl))-OtBu (1.91 g, 2.51 mmol) and N-hydroxysuccinimide (0.32 g, 2.76 mmol) were dissolved in dichloromethane (40 mL). Dicyclohexylcarbodiimide (0.62 g, 3.01 mmol) was subsequently added, and the reaction was continued overnight at ambient temperature. The reaction was then filtered to remove the dicyclohexylurea, and the filtrate was diluted with dichloromethane. The organic layer was extracted with saturated sodium bicarbonate (3x) and washed with brine (1x) before drying over anhydrous magnesium sulfate. Filtration and evaporation of the solvent under reduced pressure revealed a foam which was immediately used without further purification. The active ester (1.05 g, 1.27 mmol) was added to a suspension of Gly-dmen hydrochloride (0.23 g, 1.27 mmol) in dichloromethane (25 mL) in the presence of triethylamine (0.13 g, 1.27 mmol). After adding DMF (2 mL) to improve solubility, the reaction was continued overnight at room temperature before diluting with dichloromethane. The organic layer was extracted with saturated sodium bicarbonate (3x), water (1x), and brine (1x) before drying over anhydrous magnesium sulfate. Filtration and evaporation of the solvent under reduced pressure revealed 0.99 g (88% yield) of a clear oil of sufficient purity by NMR; no further purification was performed.

Step g
Asp-L-Lys(ε-γ-L-Glu(N-α-S-THP-mercaptoacetyl)-Gly-dmen)

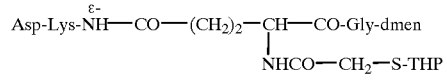

N-Boc-L-Asp(β-OtBu)-L-Lys(ε-γ-L-Glu(N-α-S-THP-mercaptoacetyl)-Gly-dmen)-OtBu (0.99, 1.11 mmol) was dissolved in 1:1 TFA/dichloromethane (4 mL each). After two hours, the solvent was removed under reduced pressure, and the residue was purified by reverse phase $C_{18}$ chromatography using 3% acetic acid/water as the mobile phase to afford 300 mg of product (34% yield).

Step h

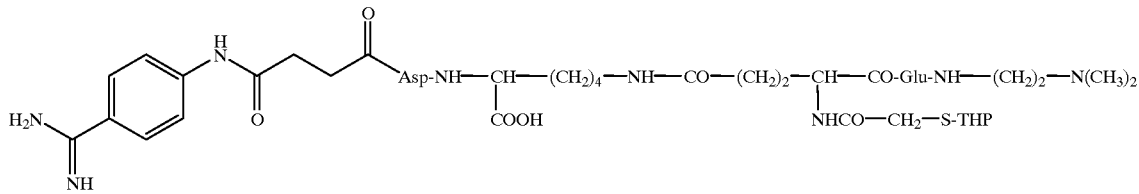

ABAS.HCl (104 mg, 0.38 mmol) was dissolved in DMF (5 mL). N-methylmorpholine (39 mg, 0.38 mmol, 0.042 mL) and isobutyl chloroformate (52 mg, 0.38 mmol) were added after cooling to 0° C. After stirring for one half hour, Asp-L-Lys(e-g-L-Glu(N-a-S-THP-mercaptoacetyl)-Gly-dmen) (290, 0.36 mmol) and N-methylmorpholine (73 mg, 0.72 mmol) were added, and the reaction was continued overnight at ambient temperature. The solvent was removed under reduced pressure, and the residue was partially purified by reverse phase $C_{18}$ flash chromatography using 30% acetonitrile/3% acetic acid/water as an isocratic eluent ($R_f$= 0.23, 60% acetonitrile/3% acetic acid/water). A final HPLC purification was performed to remove the remaining trace impurities.

EXAMPLE 32

This Example describes the stepwise preparation of a compound having the structure and the reaction was stirred for one hour before adding potassium carbonate (1.38 g, 10.0 mmol). After stirring for another hour, water (10 mL) was added. Finally, after a total reaction time of four hours, the solvent was removed under reduced pressure. The residue was redissolved in ethyl acetate, and the organic solution was extracted with 10% sodium bicarbonate. The organic layer was set aside, and the aqueous layer was extracted with ethyl acetate (2x). The combined ethyl acetate layer was then extracted with 10% sodium bicarbonate (2x) and washed with brine (1x) before drying over anhydrous magnesium sulfate. Filtration and evaporation of the solvent under reduced pressure revealed an oily semi-solid. The crude material was purified by preadsorbing onto reverse phase $C_{18}$ and dry loading this mixture onto a reverse phase $C_{18}$ column packed with 25% acetonitrile/water. Elution was accomplished with a gradient from 25% acetonitrile to 50% acetonitrile to provide 200 mg of product (16% yield). Mass Spec. (ESI) 621 (M+1).

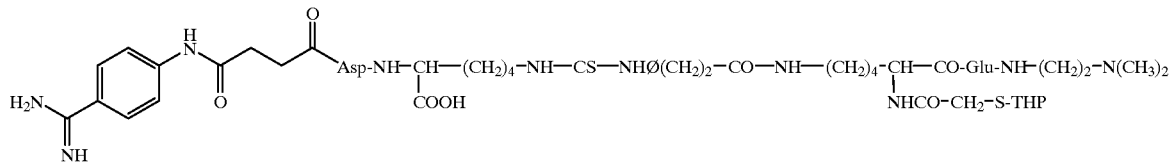

Step a
S-THP-mercaptoacetyl-L-Lys(ε-(4-propionylphenyl isothiocyanate)-Gly-dmen

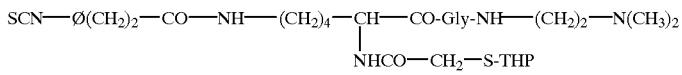

S-THP-mercaptoacetyl-L-Lys-Gly-dmen.2TFA (1.32 g, 2.00 mmol) was dissolved in acetonitrile (25 mL). A solution of 3-(p-isothiocyanato-phenyl)propionyl chloride (0.677 g, 3.00 mmol) in chloroform (25 mL) was subsequently added, Step b
ABAS-L-Asp-L-Lys phenylpropionyl-ε-L-Lys(N-α-S-THP-mercaptoacetyl)-Gly-dmen Thiourea

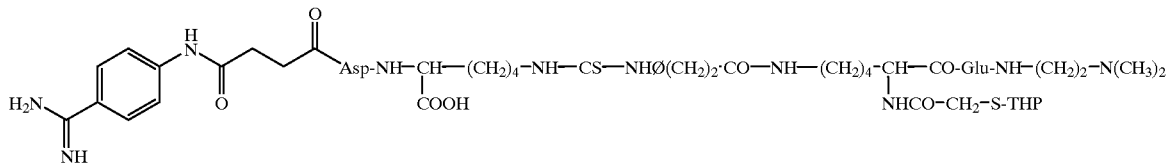

S-THP-mercaptoacetyl-L-Lys(ε-(4-propionylphenyl isothiocyanate)-Gly-dmen (42 mg, 68 mmol) was dissolved in DMF (1.5 mL). ABAS-L-Asp-L-Lys.2TFA (96 mg, 140 mmol) and triethylamine (50 ml) were subsequently added, and the reaction was continued overnight at ambient temperature. The solvent was removed under reduced pressure, and the residue was dissolved 10% acetonitrile/water and loaded onto a reverse phase $C_{18}$ column packed with the same solvent system. A gradient elution from 10% acetonitrile to 20% acetonitrile resulted in the isolation of 28 mg of product (38% yield). Mass Spec. (ESI) 1099 (M+1).

EXAMPLE 33

A 99m-Tc labeled molecule consisting of an N3S-chelate chemically linked to a peptidominmatic moiety which has high affinity for the GpIIb/IIIa receptor expressed on activated platelets was prepared from an instant kit and 99m-pertechnatate with radiochemical purity >95% and is stable for up to 6 hours. Studies in normal volunteers showed rapid blood clearance ($t_{1/2}$=11±4 min) and extensive liver uptake (31.7±1.6% i.d. 30 min p.i.). The purpose of this procedure was to assess the labeled compound for imaging fresh thrombi in humans. We studied seven patients (3 males, 4 females, 58±12 yr) with diagnosis of deep vein thrombosis based on pain of one lower limb, fibrin degradation products (D-Dimer) >2.3 μg/ml, and positive compression ultra sonography examination. The labeled compound (15–20 mCi Tc-99m) was administered to each patient within 2 hours of enrollment. Whole body images were acquired at 30 and 60 minutes p.i. Activity ratios between the affected and contralateral limbs were calculated. Tracer accumulation was in all cases consistent with the diagnosis. Affected/contralateral limb activity ratios were 1.82±0.58 at 30 minutes and 1.96±0.73 at 60 minutes (in normals=0.98±0.004 and 0.99±0.005 respectively). These results indicate that members of this class of Tc-99m compounds have potential for the imaging of fresh thrombi.

What is claimed is:

1. A radiopharmaceutical capable of localizing at a site of thrombus containing activated platelets within a mammalian body, the radiopharmaceutical comprising a linear peptidomimetic containing ligand capable of specifically binding to platelets in the thrombus and a radionuclide complexed with the peptidomimetic containing ligand wherein the peptidomimetic containing ligand has the structure:

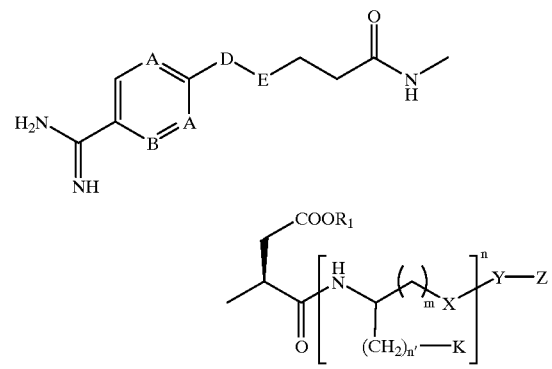

where A is —CH— or —N—, and B is —CH— or —N—, with the proviso that when A is —N—, B is —CH—, and when B is —N—, then A is —CH—; —D—E— is —$CH_2$—$CH_2$—, or —NHCO— with the proviso that when A is —N—, then —D—E is —$CH_2$—$CH_2$—, and when B is —N—, then —D—E is —NHCO—; $R_1$ is hydrogen, lower alkyl, or acyloxyalkyl; K is hydrogen, carboxyl, lower alkyl, aralkyl, substituted or unsubstituted aromatic, or an alkylene or substituted alkylene substituted with one of the following substituents: primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; X is NH, CO, S, or O; Y is NH, CO, CS, CONH, CSNH, NHCO, NHCS, CONHØ($CH_2$)$_{1-4}$CONH, CONH($CH_2$)$_{1-4}$CONH, CSNHØ($CH_2$)$_{1-4}$CONH, or CSNH($CH_2$)$_{1-4}$CONH, with the proviso that X and Y are different except when X is S, and when X is O, Y is CO, and when X is S, Y is S, CO or CS, and when X is NH, Y is CO, CONH, CSNH, CONHØ($CH_2$)$_{1-4}$CONH, CONH($CH_2$)$_{1-4}$CONH, CSNHØ($CH_2$)$_{1-4}$CONH, or CSNH($CH_2$)$_{1-4}$CONH, and when X is NH, Y is not NH, NHCO or NHCS, and when X is CO, Y is NH, O or S, and when X is CO, Y is not CO, CS, CONH, CSNH, CONHØ($CH_2$)$_{1-4}$CONH, CONH($CH_2$)$_{1-4}$CONH, CSNHØ($CH_2$)$_{1-4}$CONH, or CSNH($CH_2$)$_{1-4}$CONH; n is 0–5; n' is 0 or 1; m is 0–10; and Z is a metal binding group capable of covalently binding a radionuclide.

2. The radiopharmaceutical of claim 1 wherein Z is $R_2$-NH-CH($R_3$)-[CH($R_4$)]$_{p''}$—CO—NH—$AA_1$—NH(CH-L)$_{p'''}$—(CH-L')$_{p''''}$-L'' where $R_2$ is COCH($R_5$)-S-$R_6$; $R_5$ is H, —($CH_2$)$_p$-$R_7$; p is 1–5; $R_7$ is a hydrogen, primary amine, secondary amine, cyclic or acyclic tertiary amine, carboxyl, ester, hydroxyl, ether, thiol, thioether, guanido, or an imine; R6 is a hydrogen, aliphatic or aromatic acyl, acetamidoalkyl, benzamidoalkyl, unsubstituted or substituted tetrahydropyranyl, unsubstituted or substituted tetrahydrofuranyl, or alkoxyalkyl; $R_3$ is $(CH_2)_{p'}$-Q where p' is 0–6, Q is hydrogen, alkylene or substituted alkylene, aryl or substituted aryl group for attachment to Y; $R_4$ is $(CH_2)_s$-T where s is 0–6, T is hydrogen, alkylene or substituted alkylene,, aryl or substituted aryl group for attachment to Y; p'' is 0,1 if p'' is 1 only one of the groups defined under Q or T is attached to Y; $AA_1$ is any natural or unnatural α-amino acid or β-amino acid; L, L'=is a hydrogen, carboxyl, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; p''' is 0–3; p'''' is 0–3; L'' is a hydrogen, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl.

3. The radiopharmaceutical of claim 2 wherein A and B are CH.

4. The radiopharmaceutical of claim 3 wherein D-E is NHCO.

5. The radiopharmaceutical of claim 4 wherein the peptidomimetic containing ligand has the structure:

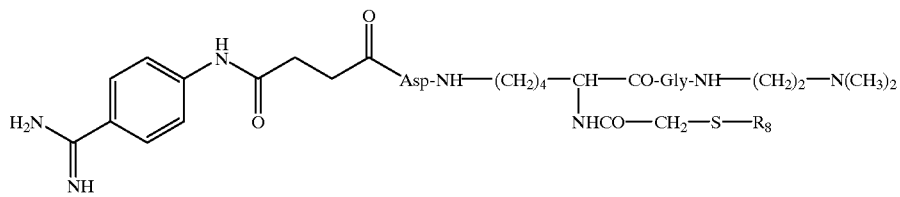

where $R_8$ is a suitable sulfur protecting group.

6. The radiopharmaceutical of claim 4 wherein the peptidomimetic containing ligand has the structure:

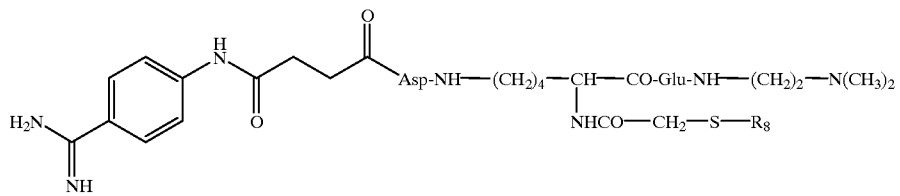

where $R_8$ is a suitable sulfur protecting group.

7. The radiopharmaceutical of claim 4 wherein the peptidomimetic containing ligand has the structure:

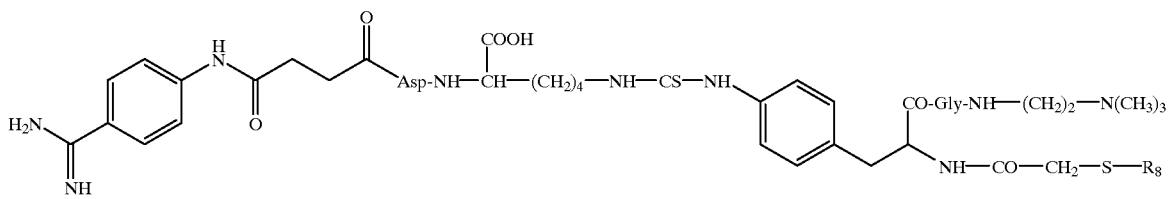

where R$_8$ is a suitable sulfur protecting group.

8. The radiopharmaceutical of claim 4 wherein the peptidomimetic containing ligand has the structure:

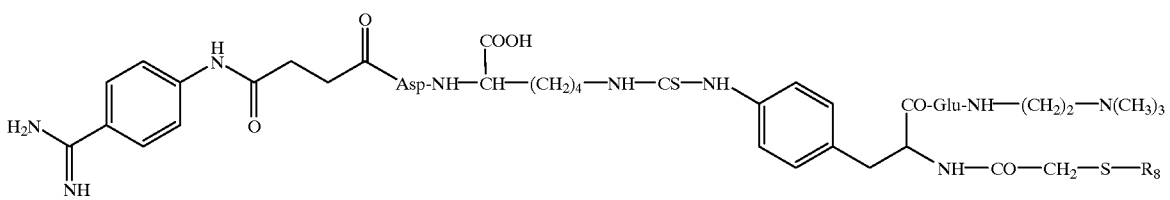

where R$_8$ is a suitable sulfur protecting group.

9. The radiopharmaceutical of claim 4 wherein the peptidomimetic containing ligand has the structure:

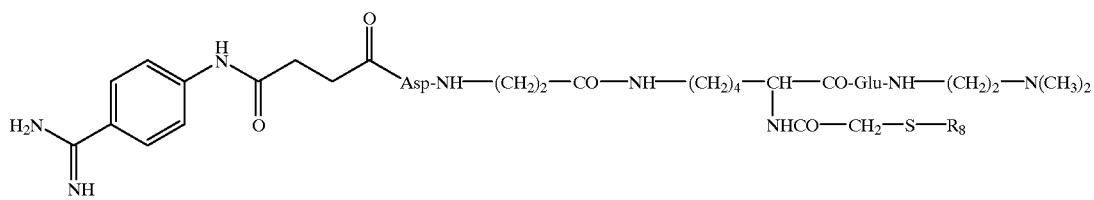

where R$_8$ is a suitable sulfur protecting group.

10. The radiopharmaceutical of claim 4 wherein the peptidomimetic containing ligand has the structure:

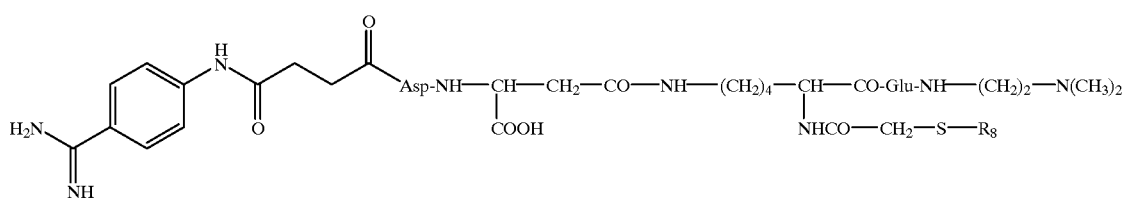

where R$_8$ is a suitable sulfur protecting group.

11. The radiopharmaceutical of claim 4 wherein the peptidomimetic containing ligand has the structure:

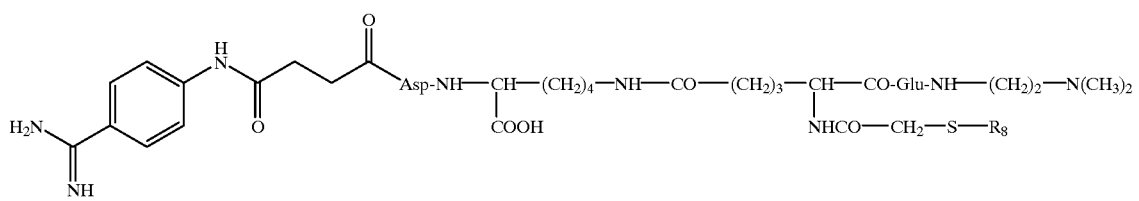

where $R_8$ is a suitable sulfur protecting group.

12. The radiopharmaceutical of claim 4 wherein the peptidomimetic containing ligand has the structure:

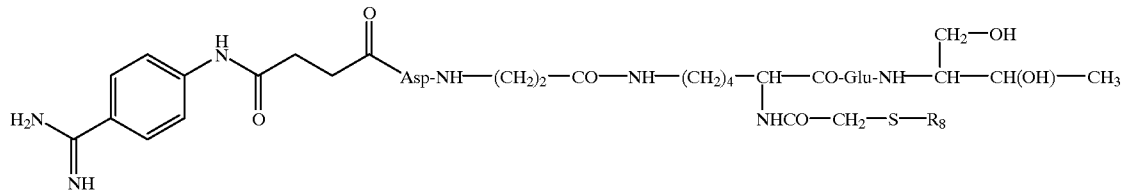

where $R_8$ is a suitable sulfur protecting group.

13. The radiopharmaceutical of claim 4 wherein the peptidomimetic containing ligand has the structure:

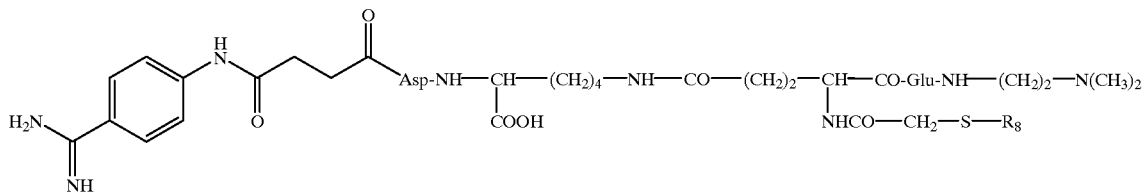

where $R_8$ is a suitable sulfur protecting group.

14. The radiopharmaceutical of claim 4 wherein the complex of the radionuclide and the peptidomimetic containing ligand has the structure:

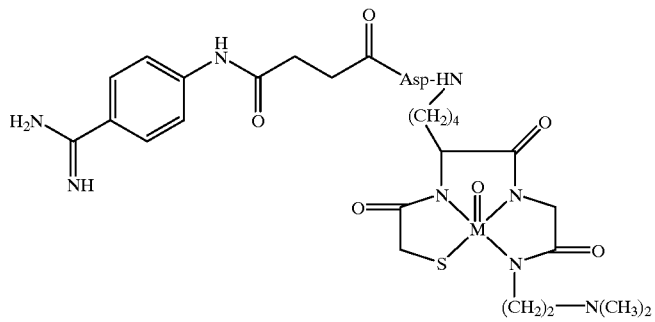

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

15. The radiopharmaceutical of claim 4 wherein the complex of the radionuclide and the peptidomimetic containing ligand has the structure:

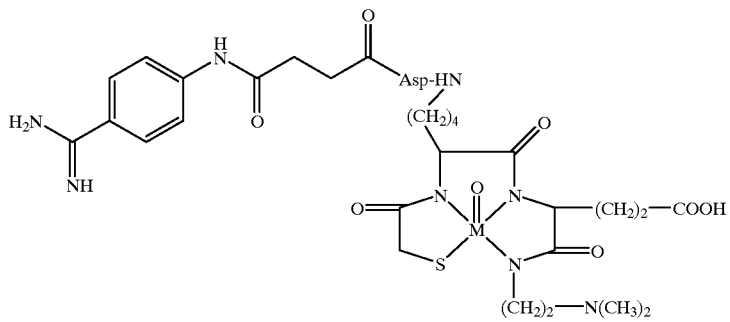

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

16. The radiopharmaceutical of claim 4 wherein the complex of the radionuclide and the peptidomimetic containing ligand has the structure:

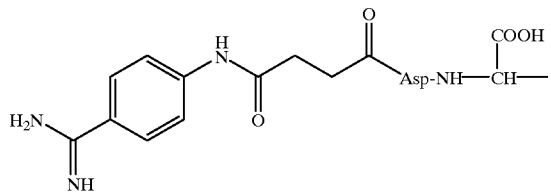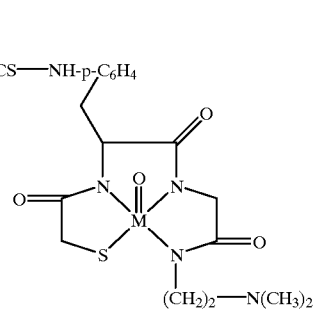

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

17. The radiopharmaceutical of claim 4 wherein the complex of the radionuclide and the peptidomimetic containing ligand has the structure:

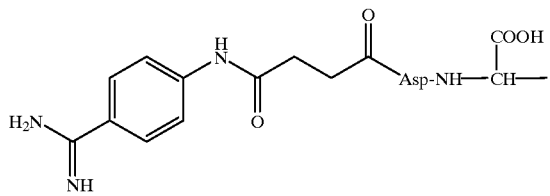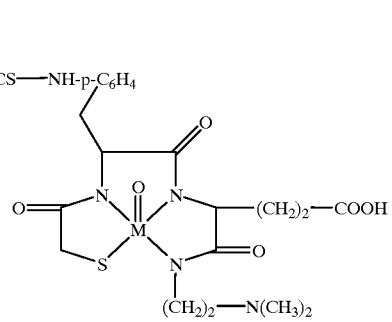

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

18. The radiopharmaceutical of claim 4 wherein the complex of the radionuclide and the peptidomimetic containing ligand has the structure:

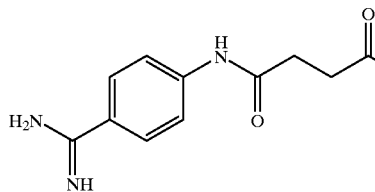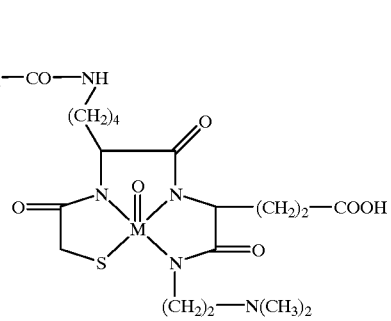

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

19. The radiopharmaceutical of claim 4 wherein the complex of the radionuclide and the peptidomimetic containing ligand has the structure:

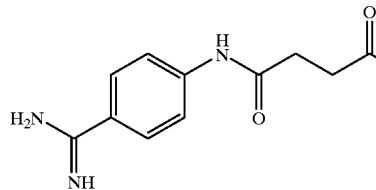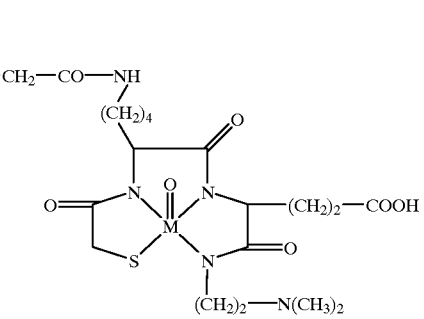

where M is selected from the group consisting of 67Ga, 111In, 99mTc, 169Yb, 186Re, 90Y, 67Cu, 186Re, 188Re, 169Er, 121 Sn, 127Te, 143Pr, 198Au, 109Pd, 165Dy, 32P, 142Pr, and 153Sm.

20. The radiopharmaceutical of claim 4 wherein the complex of the radionuclide and the peptidomimetic containing ligand has the structure:

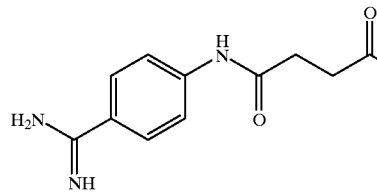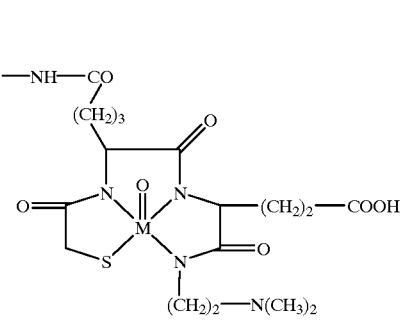

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

21. The radiopharmaceutical of claim 4 wherein the complex of the radionuclide and the peptidomimetic containing ligand has the structure:

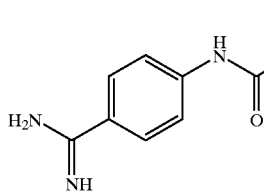
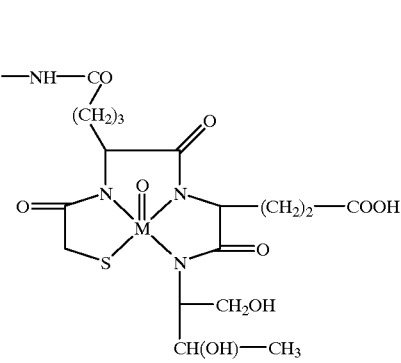

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

22. The radiopharmaceutical of claim 4 wherein the complex of the radionuclide and the peptidomimetic containing ligand has the structure:

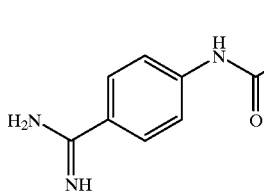
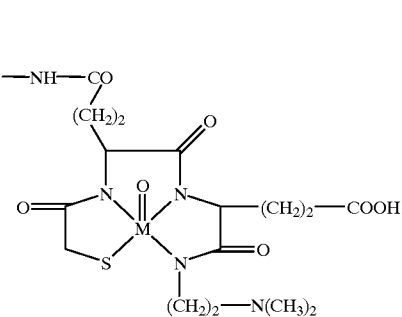

where M is selected from the group consisting of 67Ga, 111In, 99mTc, 169Yb, 186Re, 90Y, 67Cu, 186Re, 188Re, 169Er, 121Sn, 127Te, 143Pr, 198Au, 109Pd, 165Dy, 32P, 142Pr, and 153Sm.

23. A ligand composition for preparing a radiopharmaceutical having the structure:

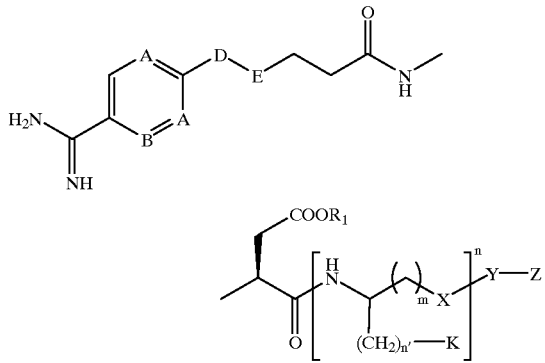

where A is —CH— or —N—, and B is —CH— or —N—, with the proviso that when A is —N—, B is —CH—, and when B is —N—, then A is —CH—; —D—E— is —CH$_2$—CH$_2$—, or —NHCO— with the proviso that when A is —N—, then —D—E is —CH$_2$—CH$_2$—, and when B is —N—, then —D—E is —NHCO—; R$_1$ is hydrogen, lower alkyl, or acyloxyalkyl; K is hydrogen, carboxyl, lower alkyl, aralkyl, substituted or unsubstituted aromatic, or an alkylene or substituted alkylene substituted with one of the following substituents: primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; X is NH, CO, S, or O; Y is NH, CO, CS, CONH, CSNH, NHCO, NHCS, CONHØ(CH$_2$)$_{1-4}$CONH, CONH(CH$_2$)$_{1-4}$CONH, CSNHØ(CH$_2$)$_{1-4}$CONH, or CSNH (CH$_2$)$_{1-4}$CONH, with the proviso that X and Y are different except when X is S, and when X is O, Y is CO, and when X is S, Y is S, CO or CS, and when X is NH, Y is CO, CONH, CSNH, CONHØ(CH$_2$)$_{1-4}$CONH, CONH(CH$_2$)$_{1-4}$ CONH, CSNHØ(CH$_2$)$_{1-4}$CONH, or CSNH(CH$_2$)$_{1-4}$ CONH, and when X is NH, Y is not NH, NHCO or NHCS, and when X is CO, Y is NH, O or S, and when X is CO, Y is not CO, CS, CONH, CSNH, CONHØ(CH$_2$)$_{1-4}$CONH, CONH(CH$_2$) 1-4CONH, CSNHØ(CH$_2$)$_{1-4}$CONH, or CSNH(CH$_2$)$_{1-4}$CONH; n is 0–5; n' is 0 or 1; m is 0–10; and Z is a metal binding group capable of covalently binding a radionuclide.

24. The ligand of claim 23 wherein Z is

R$_2$—NH—CH(R$_3$)—[CH(R$_4$)]$_{p''}$—CO—NH—AA$_1$—NH(CH-L)$_{n''''}$—(CH-L)$_{n''''}$-L'' where R$_2$ is COCH (R$_5$)—S—R$_6$; R$_5$ is H, —(CH$_2$)$_p$—R$_7$; p is 1–5; R$_7$ is a hydrogen, primary amine, secondary amine, cyclic or acyclic tertiary amine, carboxyl, ester, hydroxyl, ether, thiol, thioether, guanido, or an imine; R$_6$ is a hydrogen, aliphatic or aromatic acyl, acetamidoalkyl, benzamidoalkyl, unsubstituted or substituted tetrahydropyranyl, unsubstituted or substituted tetrahydrofuranyl, or alkoxyalkyl; $R_3$ is $(CH_2)_{p'}$—Q where p' is 0–6, Q is hydrogen, alkylene or substituted alkylene, aryl or substituted aryl group for attachment to Y; $R_4$ is $(CH_2)_s$—T where s is 0–6, T is hydrogen, alkylene or 20 substituted alkylene,, aryl or substituted aryl group for attachment to Y; p" is 0, 1 if p" is 1 only one of the groups defined under Q or T is attached to Y; $AA_1$ is any natural or unnatural α-amino acid or β-amino acid; L, L'=is a hydrogen, carboxyl, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; p'" is 0–3; p"" is 0–3; L" is a hydrogen, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, irnine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl.

25. The ligand of claim 24 wherein A and B are CH.
26. The ligand of claim 25 wherein D-E is NHCO.
27. The ligand of claim 26 having the structure:

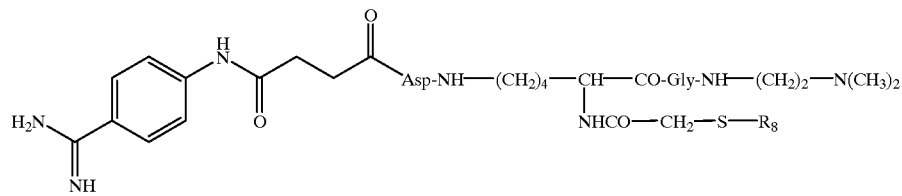

where $R_8$ is a suitable sulfur protecting group.

28. The ligand of claim 26 having the structure:

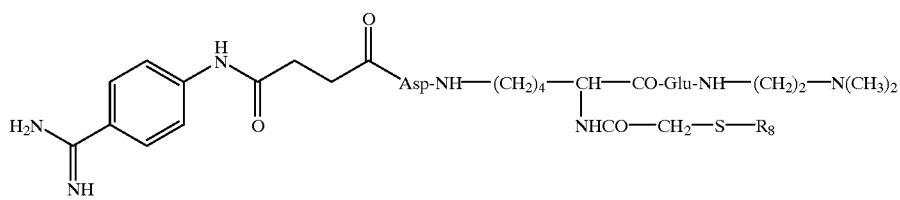

where $R_8$ is a suitable sulfur protecting group.

29. The ligand of claim 26 having the structure:

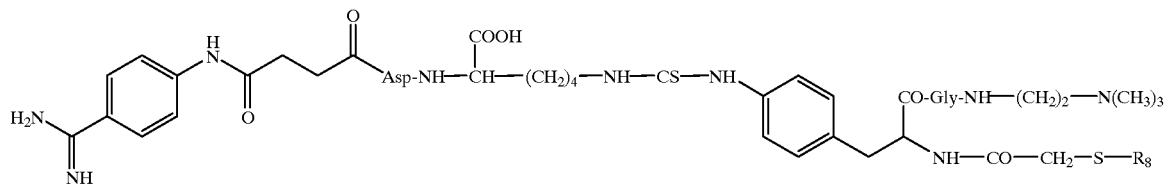

where $R_8$ is a suitable sulfur protectng group.

30. The ligand of claim 26 having the structure:

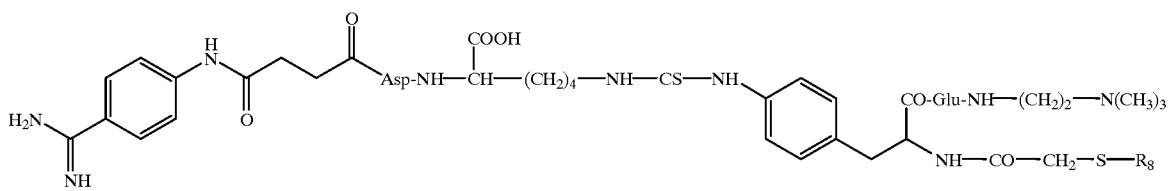

where $R_8$ is a suitable sulfur protecting group.

31. The ligand of claim 26 having the structure:

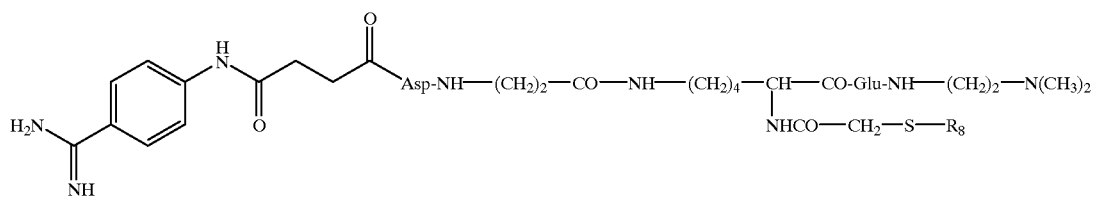

where $R_8$ is a suitable sulfur protecting group.

32. The ligand of claim 26 having the structure:

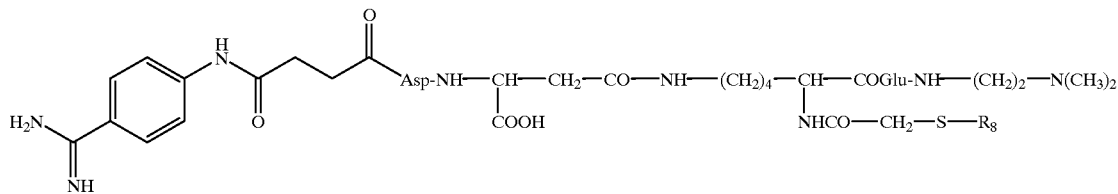

where $R_8$ is a suitable sulfur protecting group.

33. The ligand of claim 26 having the structure:

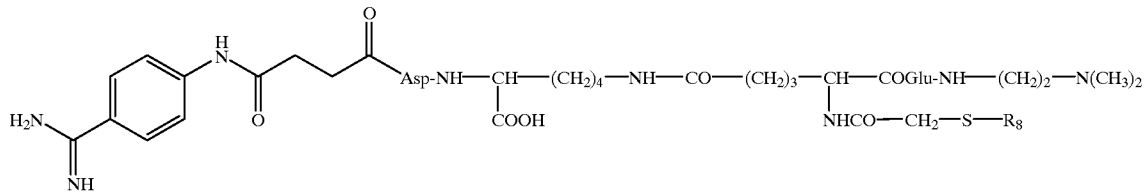

where $R_8$ is a suitable sulfur protecting group.

34. The ligand of claim 26 having the structure:

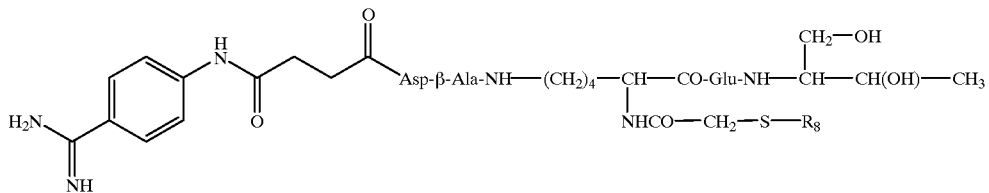

where $R_8$ is a suitable sulfur protecting group.

35. The ligand of claim 26 having the structure:

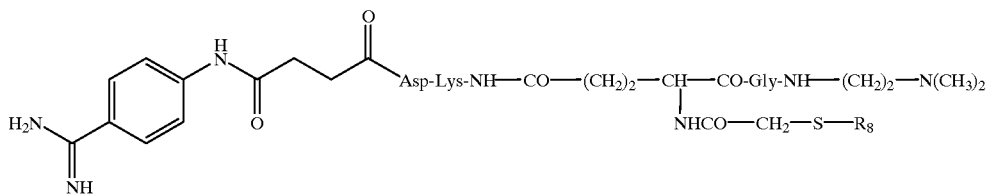

where $R_8$ is a suitable sulfur protecting group.

36. A kit for a radiopharmaceutical composition comprising a container containing a selected amount of a linear peptidomimetic containing ligand in a pharmaceutically acceptable vehicle and a sufficient amount of a reducing reagent to permit labeling of the composition with a selected radionuclide wherein the peptidomimetic containing ligand has the structure:

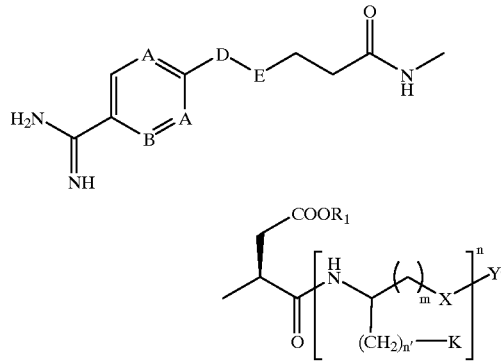

where A is —CH— or —N—, and B is —CH— or —N—, with the proviso that when A is —N—, B is —CH—, and when B is —N—, then A is —CH—; —D—E— is —CH$_2$—CH$_2$—, or —NHCO— with the proviso that when A is —N—, then —D—E is —CH$_2$—CH$_2$—, and when B is —N—, then —D—E is NHCO—; $R_1$ is hydrogen, lower alkyl, or acyloxyalkyl; K is hydrogen, carboxyl, lower alkyl, aralkyl, substituted or unsubstituted aromatic, or an alkylene or substituted alkylene substituted with one of the following substituents: primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; X is NH, CO, S, or O; Y is NH, CO, CS, CONH, CSNH, NHCO, NHCS, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH, with the proviso that X and Y are different except when X is S, and when X is O, Y is CO, and when X is S, Y is S, CO or CS, and when X is NH, Y is CO, CONH, CSNH, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$ CONH, and when X is NH, Y is not NH, NHCO or NHCS, and when X is CO, Y is NH, O or S, and when X is CO, Y is not CO, CS, CONH, CSNH, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH; n is 0–5; n' is 0 or 1; m is 0–10; and Z is a metal binding group capable of covalently binding a radionuclide.

37. The kit of claim 36 wherein Z is $R_2$—NH—CH($R_3$)—[CH($R_4$)]$_{p''}$—CO—NH—AA$_1$—NH(CH-L)$_{n''''}$—(CH-L)$_{n''''}$L" where $R_2$ is COCH($R_5$)-S-$R_6$; $R_5$ is H, —(CH$_2$)$_p$—$R_7$; p is 1–5; $R_7$ is a hydrogen, primary amine, secondary amine, cyclic or acyclic tertiary amine, carboxyl, ester, hydroxyl, ether, thiol, thioether, guanido, or an imine; $R_6$ is a hydrogen, aliphatic or aromatic acyl, acetamidoalkyl, benzamidoalkyl, unsubstituted or substituted tetrahydropyranyl, unsubstituted or substituted tetrahydrofuranyl, or alkoxyalkyl; $R_3$ is (CH$_2$)$_{p'}$—Q where p' is 0–6, Q is hydrogen, alkylene or substituted alkylene, aryl or substituted aryl group for attachment to Y; $R_4$ is (CH$_2$)$_s$-T where s is 0–6, T is hydrogen, alkylene or substituted alkylene,, aryl or substituted aryl group for attachment to Y; p" is 0,1 if p" is 1 only one of the groups defined under Q or T is attached to Y; AA$_1$ is any natural or unnatural α-amino acid or β-amino acid; L, L'=is a hydrogen, carboxyl, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; p'" is 0–3; p"" is 0–3; L" is a hydrogen, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl.

38. The kit of claim 37 wherein A and B are CH.

39. The kit of claim 38 wherein D-E is NHCO.

40. The kit of claim 39 wherein the peptidomimetic containing ligand has the structure:

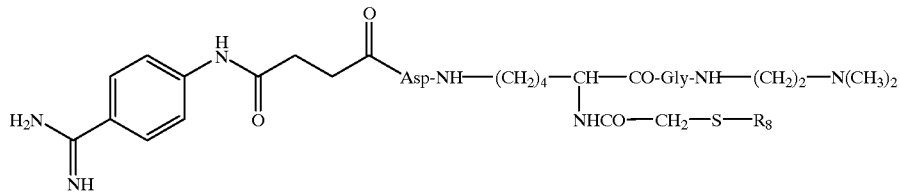

where $R_8$ is a suitable sulfur protecting group.

41. The kit of claim 39 wherein the peptidomimetic containing ligand has the structure:

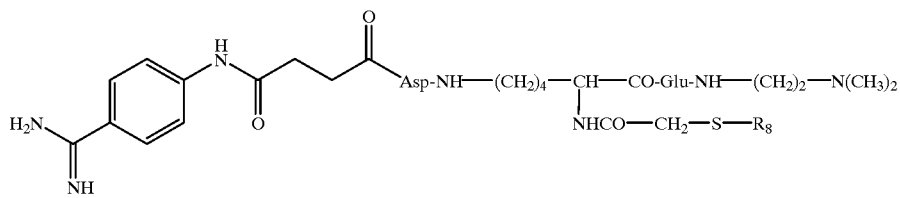

where $R_8$ is a suitable sulfur protecting group.

42. The kit of claim 39 wherein the peptidomimetic containing ligand has the structure:

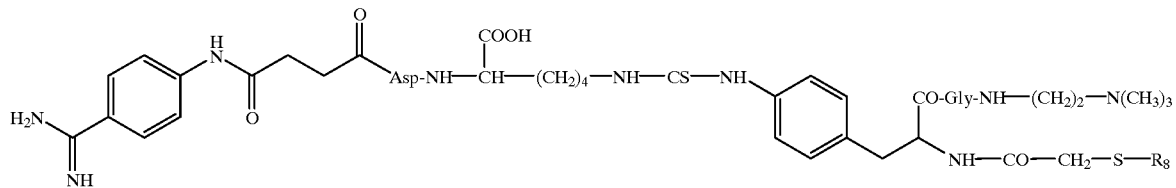

where $R_8$ is a suitable sulfur protecting group.

43. The kit of claim 39 wherein the peptidomimetic containing ligand has the structure:

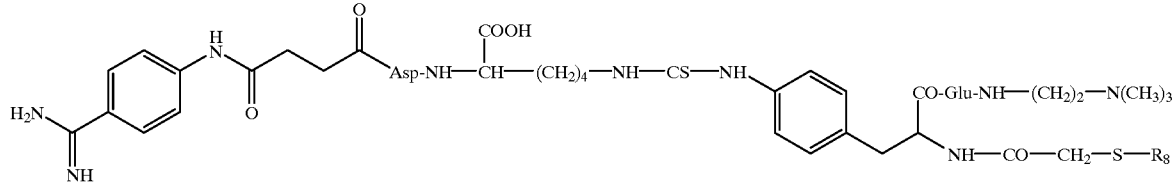

where $R_8$ is a suitable sulfur protecting group.

44. The kit of claim 39 wherein the peptidomimetic containing ligand has the structure:

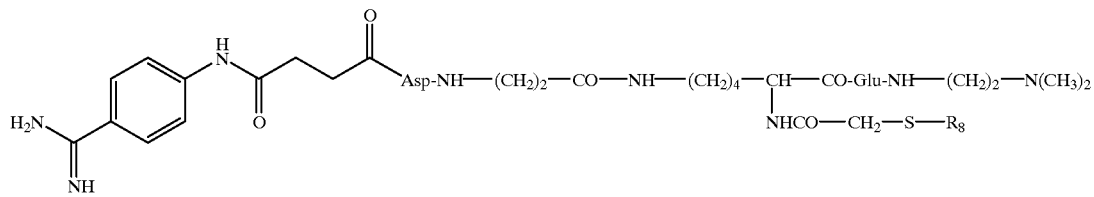

where R₈ is a suitable sulfur protecting group.

45. The kit of claim 39 wherein the peptidomimetic containing ligand has the structure:

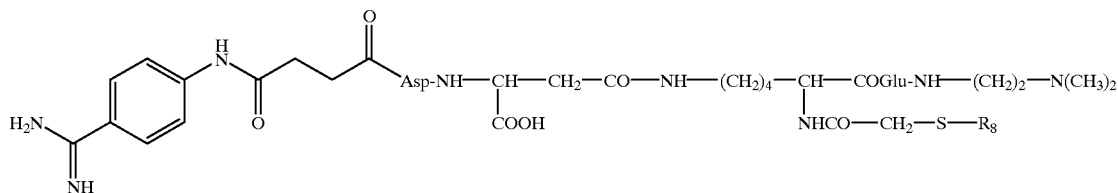

where R₈ is a suitable sulfur protecting group.

46. The kit of claim 39 wherein the peptidomimetic containing ligand has the structure:

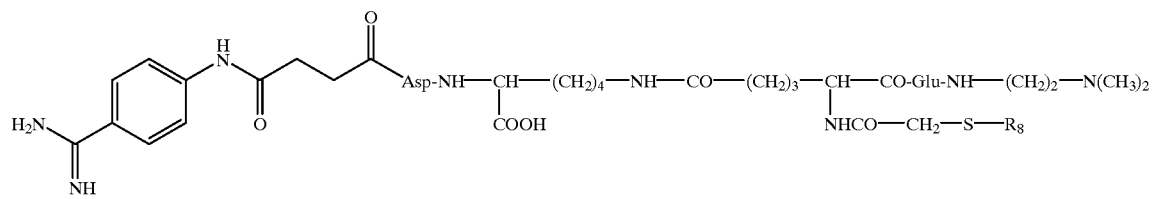

where R₈ is a suitable sulfur protecting group.

47. The kit of claim 39 wherein the peptidomimetic containing ligand has the structure:

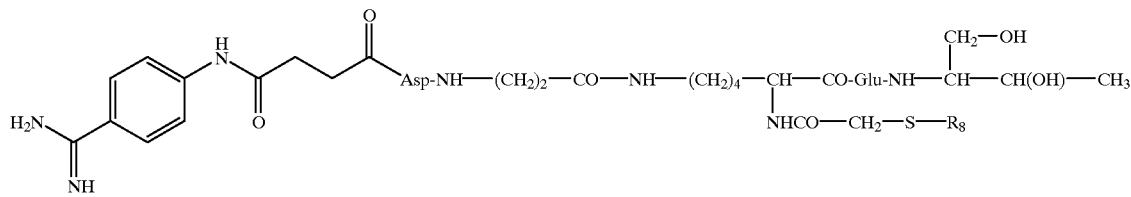

where R₈ is a suitable sulfur protecting group.

48. The kit of claim 39 wherein the peptidomimetic containing ligand has the structure:

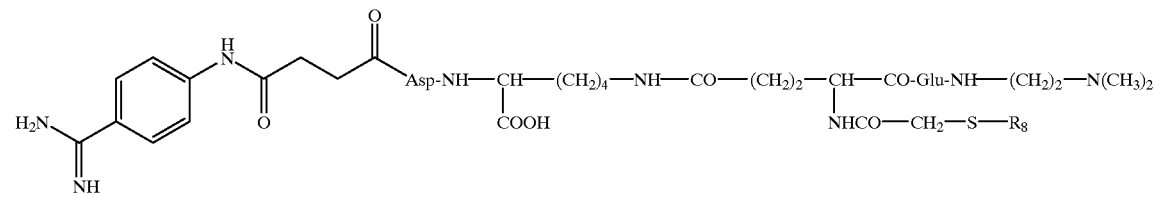

where $R_8$ is a suitable sulfur protecting group.

49. A method for imaging a site of thrombus comprising administering a diagnostically effective amount of a linear peptidomimetic containing ligand complexed with a diagnostic radionuclide and detecting the radionuclide localized at the site of thrombus wherein the peptidomimetic containing ligand prior to complexation with the radionuclide has the structure:

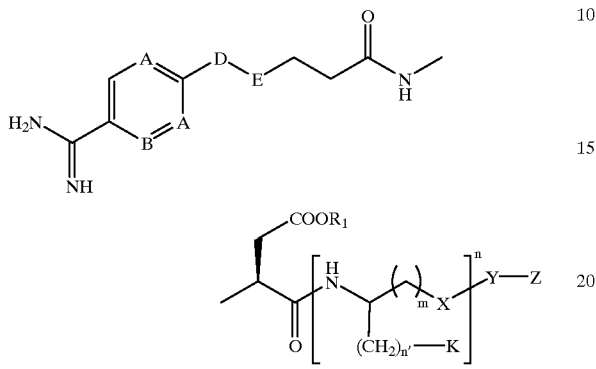

where A is —CH— or —N—, and B is —CH— or —N—, with the proviso that when A is —N—, B is —CH—, and when B is —N—, then A is —CH—; —D—E— is —CH$_2$—CH$_2$—, or —NHCO— with the proviso that when A is —N—, then —D—E is -CH$_2$-CH$_2$-, and when B is —N—, then —D—E is NHCO—; $R_1$ is hydrogen, lower alkyl, or acyloxyalkyl; K is hydrogen, carboxyl, lower alkyl, aralkyl, substituted or unsubstituted aromatic, or an alkylene or substituted alkylene substituted with one of the following substituents: primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; X is NH, CO, S, or O; Y is NH, CO, CS, CONH, CSNH, NHCO, NHCS, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH, with the proviso that X and Y are different except when X is S, and when X is O, Y is CO, and when X is S, Y is S, CO or CS, and when X is NH, Y is CO, CONH, CSNH, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH, and when X is NH, Y is not NH, NHCO or NHCS, and when X is CO, Y is NH, O or S, and when X is CO, Y is not CO, CS, CONH, CSNH, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH; n is 0–5; n' is 0 or 1; m is 0–10; and Z is a metal binding group capable of covalently binding a radionuclide.

50. The method of claim 49 wherein Z is $R_2$—NH—CH($R_3$)-[CH($R_4$)]$_{p'''}$—CO—NH—AA$_1$—NH(CH-L)$_{p''''}$—(CH-L')$_{p''''}$-L" where $R_2$ is COCH($R_5$)—S—$R_6$; $R_5$ is H, —(CH$_2$)$_p$—$R_7$; p is 1–5; $R_7$ is a hydrogen, primary amine, secondary amine, cyclic or acyclic tertiary amine, carboxyl, ester, hydroxyl, ether, thiol, thioether, guanido, or an imine; $R_6$ is a hydrogen, aliphatic or aromatic acyl, acetamidoalkyl, benzamidoalkyl, unsubstituted or substituted tetrahydropyranyl, unsubstituted or substituted tetrahydrofuranyl, or alkoxyalkyl; $R_3$ is (CH$_2$)$_{p'}$—Q where p' is 0–6, Q is hydrogen, alkylene or substituted alkylene, aryl or substituted aryl group for attachment to Y; $R_4$ is (CH$_2$)$_s$-T where s is 0–6, T is hydrogen, alkylene or substituted alkylene,, aryl or substituted aryl group for attachment to Y; p" is 0,1 if p" is 1 only one of the groups defined under Q or T is attached to Y; AA$_1$ is any natural or unnatural α-amino acid or β-amino acid; L, L'=is a hydrogen, carboxyl, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; p''' is 0– 3; p'''' is 0–3; L" is a hydrogen, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl.

51. The method of claim 49 wherein A and B are CH.
52. The method of claim 50 wherein D-E is NHCO.
53. The method of claim 51 wherein the peptidomimetic containing ligand has the structure:

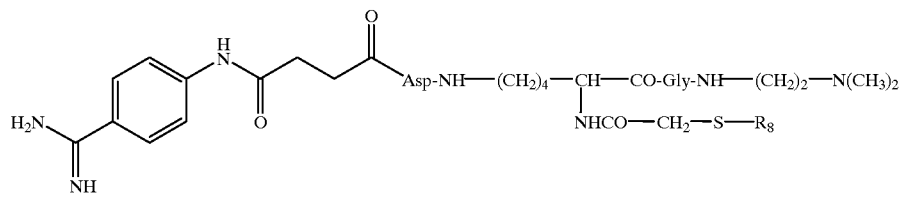

where $R_8$ is a suitable sulfur protecting group.

54. The method of claim 51 wherein the peptidomimetic containing ligand has the structure:

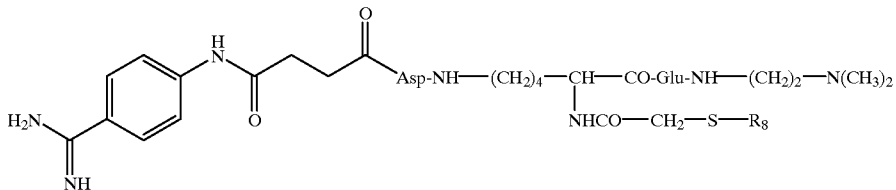

where $R_8$ is a suitable sulfur protecting group.

55. The method of claim 51 wherein the peptidomimetic containing ligand has the structure:

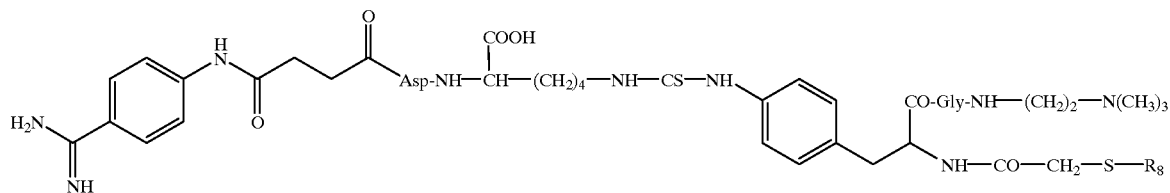

where $R_8$ is a suitable sulfur protecting group.

56. The method of claim 51 wherein the peptidomimetic containing ligand has the structure:

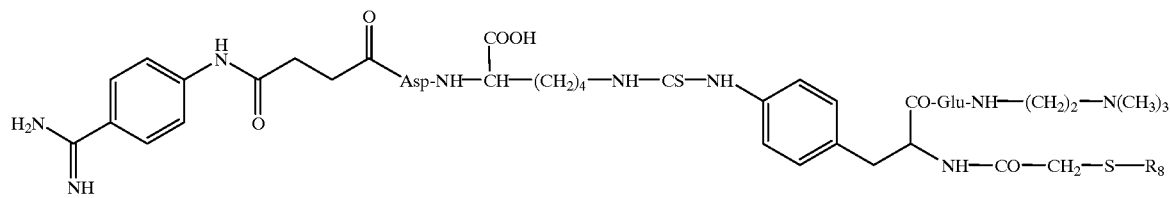

where $R_8$ is a suitable sulfur protecting group.

57. The method of claim 51 wherein the peptidomimetic containing ligand has the structure:

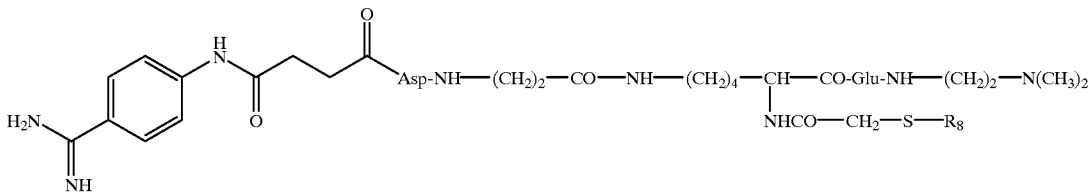

where $R_8$ is a suitable sulfur protecting group.

58. The method of claim 51 wherein the peptidomimetic containing ligand has the structure:

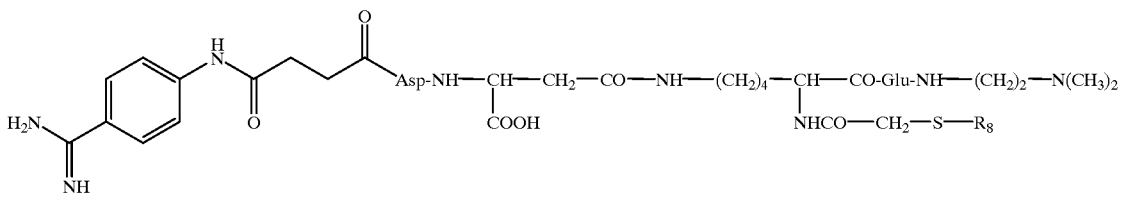

where $R_8$ is a suitable sulfur protecting group.

59. The method of claim 51 wherein the peptidomimetic containing ligand has the structure:

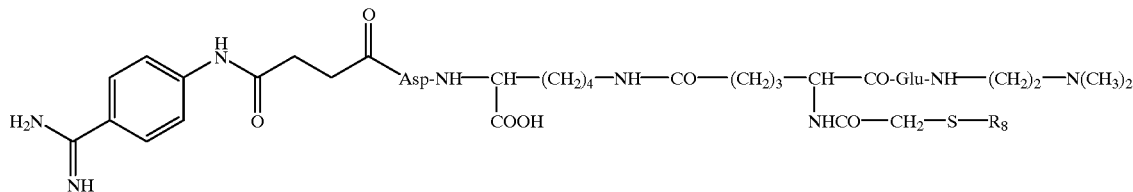

where $R_8$ is a suitable sulfur protecting group.

60. The method of claim 51 wherein the peptidomimetic containing ligand has the structure:

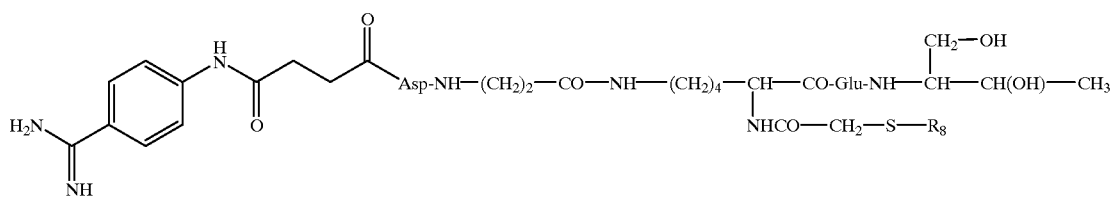

where $R_8$ is a suitable sulfur protecting group.

61. The method of claim 51 wherein the peptidomimetic containing ligand has the structure:

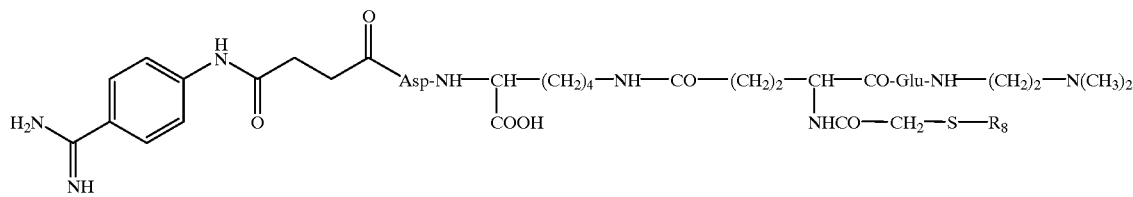

where $R_8$ is a suitable sulfur protecting group.

62. A method for providing radiotherapy to a site of thrombus comprising administering a therapeutically effective amount of a linear peptidomimetic containing ligand complexed with a therapeutic radionuclide that localizes at the site of thrombus for a period of time sufficient to ablate the thrombus wherein the peptidomimetic containing ligand has the structure:

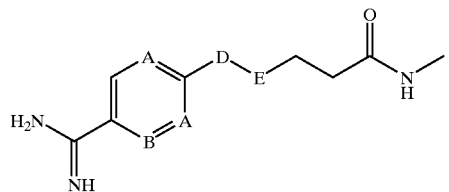

-continued

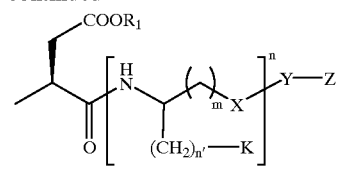

where A is —CH— or —N—, and B is —CH— or —N—, with the proviso that when A is —N—, B is —CH—, and when B is —N—, then A is —CH—; —D—E— is —CH$_2$—CH$_2$—, or —NHCO— with the proviso that when A is —N—, then —D—E is —CH$_2$—CH$_2$—, and when B is —N—, then —D—E is NHCO—; $R_1$ is hydrogen, lower alkyl, or acyloxyalkyl; K is hydrogen, carboxyl, lower alkyl, aralkyl, substituted or unsubstituted aromatic, or an alkylene or substituted alkylene substituted with one of the following substituents: primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; X is NH, CO, S, or O; Y is NH, CO, CS, CONH, CSNH, NHCO, NHCS, CONHØ(CH$_2$)$_{1-4}$CONH, CONH(CH$_2$)$_{1-4}$CONH, CSNHØ(CH$_2$)$_{1-4}$CONH, or CSNH (CH$_2$)$_{1-4}$CONH, with the proviso that X and Y are different except when X is S, and when X is O, Y is CO, and when X is S, Y is S, CO or CS, and when X is NH, Y is CO, CONH, CSNH, CONHØ(CH$_2$)$_{14}$CONH, CONH(CH$_2$)$_{1-4}$ CONH, CSNHØ(CH$_2$)$_{1-4}$CONH, or CSNH(CH$_2$)$_{1-4}$ CONH, and when X is NH, Y is not NH, NHCO or NHCS, and when X is CO, Y is NH, O or S, and when X is CO, Y is not CO, CS, CONH, CSNH, CONHØ(CH$_2$)$_{1-4}$CONH, CONH(CH$_2$)$_{1-4}$CONH, CSNHØ(CH$_2$)$_{1-4}$CONH, or CSNH(CH$_2$)$_{1-4}$CONH; n is 0–5; n' is 0 or 1; m is 0–10; and Z is a metal binding group capable of covalently binding a radionuclide.

63. The method of claim 62 wherein Z is

R$_2$—NH—CH(R$_3$)—[CH(R$_4$)]$_{p''}$—CO—NH—AA$_1$—NH(CH-L)$_{p'''}$—(CH-L')$_{p''''}$-L'' where R$_2$ is COCH (R$_5$)—S—R$_6$; R$_5$ is H, —(CH$_2$)$_p$—R$_7$; p is 1–5; R$_7$ is a hydrogen, primary amine, secondary amine, cyclic or acyclic tertiary amine, carboxyl, ester, hydroxyl, ether, thiol, thioether, guanido, or an imine; R$_6$ is a hydrogen, aliphatic or aromatic acyl, acetamidoalkyl, benzamidoalkyl, unsubstituted or substituted tetrahydropyranyl, unsubstituted or substituted tetrahydrofuranyl, or alkoxyalkyl; R$_3$ is (CH$_2$)$_{p'}$-Q where p' is 0–6, Q is hydrogen, alkylene or substituted alkylene, aryl or substituted aryl group for attachment to Y; R$_4$ is (CH$_2$)$_s$-T where s is 0–6, T is hydrogen, alkylene or substituted alkylene,, aryl or substituted aryl group for attachment to Y; p'' is 0, 1 if p'' is 1 only one of the groups defined under Q or T is attached to Y; AA$_1$ is any natural or unnatural α-amino acid or β-amino acid; L, L'=is a hydrogen, carboxyl, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl; p''' is 0–3; p'''' is 0–3; L'' is a hydrogen, lower alkyl, aralkyl, substituted or unsubstituted aromatic group, or an alkylene bearing one of the following substituents: a primary amine, secondary amine, cyclic or acyclic tertiary amine, carboxyl, ester, hydroxyl, ether, thiol, thioether, guanido, imine, aminoalkyl, monoaminoalkyl, diaminoalkyl, hydroxyalkyl, alkoxylalkyl, hydroxycarbonylalkyl, alkoxycarbonylalkyl, mercaptoalkyl, or alkylthioalkyl.

64. The method of claim 62 wherein A and B are CH.
65. The method of claim 63 wherein D-E is NHCO.
66. The method of claim 64 wherein the peptidomimetic containing ligand has the structure:

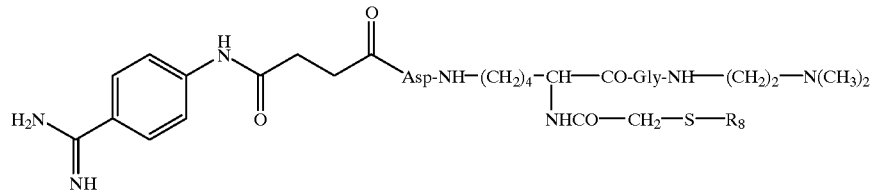

where R$_8$ is a suitable sulfur protecting group.

67. The method of claim 64 wherein the peptidomimetic containing ligand has the structure:

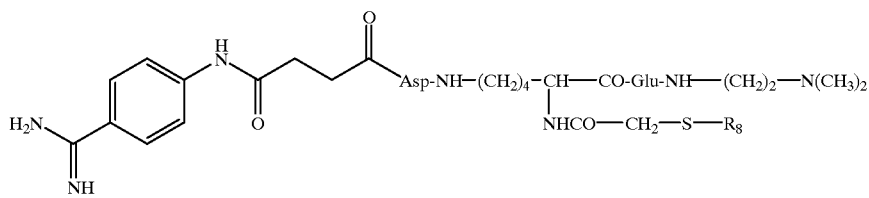

where R$_8$ is a suitable sulfur protecting group.

68. The method of claim 64 wherein the peptidomimetic containing ligand has the structure:

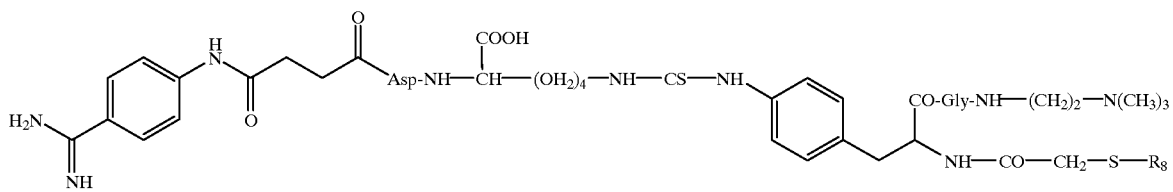

where R$_8$ is a suitable sulfur protecting group.

69. The method of claim 64 wherein the peptidomimetic containing ligand has the structure:

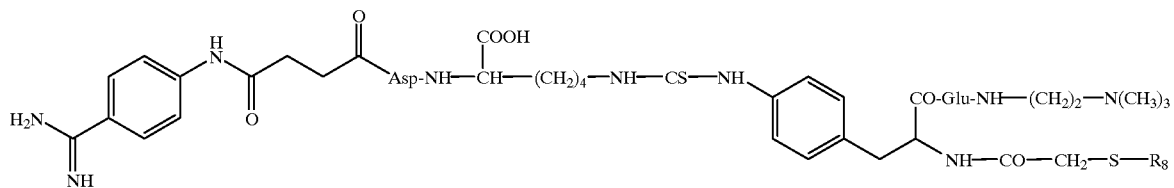

where $R_8$ is a suitable sulfur protecting group.

70. The method of claim 64 wherein the peptidomimetic containing ligand has the structure:

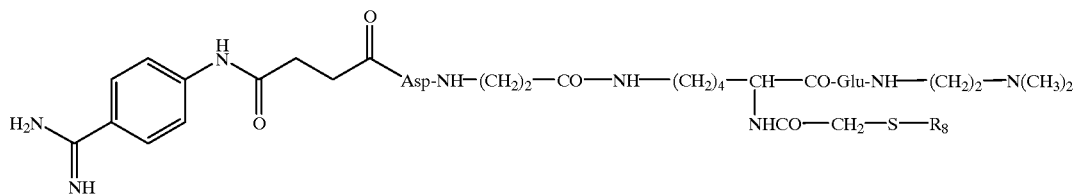

where $R_8$ is a suitable sulfur protecting group.

71. The method of claim 64 wherein the peptidomimetic containing ligand has the structure:

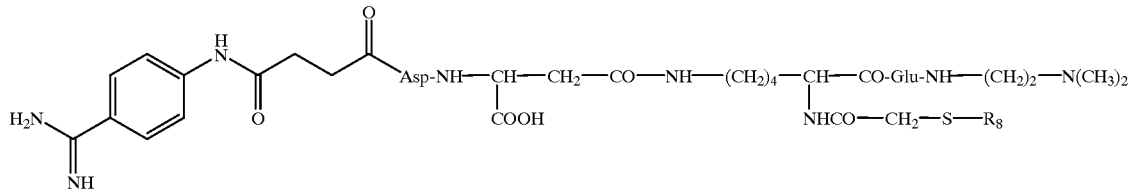

where $R_8$ is a suitable sulfur protecting group.

72. The method of claim 64 wherein the peptidomimetic containing ligand has the structure:

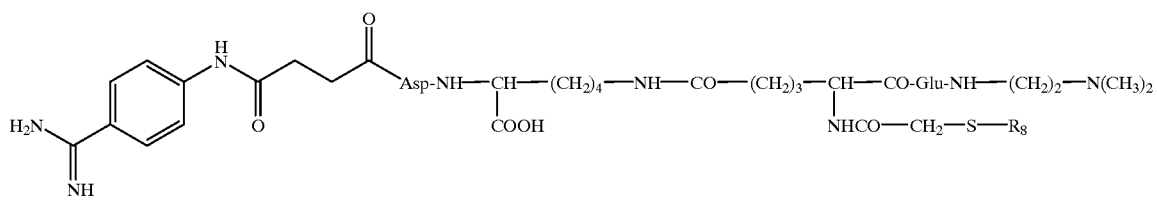

where $R_8$ is a suitable sulfur protecting group.